US010939819B2

(12) United States Patent
Kogure

(10) Patent No.: US 10,939,819 B2
(45) Date of Patent: Mar. 9, 2021

(54) ABNORMALITY DETERMINATION APPARATUS AND NON-TRANSITORY COMPUTER READABLE MEDIUM STORING PROGRAM

(71) Applicant: PARAMOUNT BED CO., LTD., Tokyo (JP)

(72) Inventor: Takamasa Kogure, Tokyo (JP)

(73) Assignee: PARAMOUNT BED CO., LTD., Tokyo (JP)

( * ) Notice: Subject to any disclaimer, the term of this patent is extended or adjusted under 35 U.S.C. 154(b) by 16 days.

(21) Appl. No.: 16/199,643

(22) Filed: Nov. 26, 2018

(65) Prior Publication Data
US 2019/0159674 A1 May 30, 2019

(30) Foreign Application Priority Data
Nov. 30, 2017 (JP) ................................. 2017-231224

(51) Int. Cl.
*A61B 5/00* (2006.01)
*A61B 5/11* (2006.01)
(Continued)

(52) U.S. Cl.
CPC .......... *A61B 5/0002* (2013.01); *A61B 5/0205* (2013.01); *A61B 5/0816* (2013.01);
(Continued)

(58) Field of Classification Search
None
See application file for complete search history.

(56) References Cited

U.S. PATENT DOCUMENTS

| 4,295,133 | A | * | 10/1981 | Vance | .................. | A61B 5/1115 |
| | | | | | | 340/573.4 |
| 4,594,583 | A | * | 6/1986 | Seko | ........................ | A61B 5/18 |
| | | | | | | 180/272 |

(Continued)

FOREIGN PATENT DOCUMENTS

| JP | 2004-159804 | 6/2004 |
| JP | 2004-159809 | 6/2004 |
| JP | 3557775 | 8/2004 |

OTHER PUBLICATIONS

Uchida, S et al., "Sleep evaluation by a newly developed PVDF sensor non-contact sheet: a comparison with standard polysomnography and wrist actigraphy", Sleep and Biological Rhythms, 2011, vol. 9, pp. 178-187.

(Continued)

*Primary Examiner* — Carl H Layno
*Assistant Examiner* — Manolis Pahakis
(74) *Attorney, Agent, or Firm* — Wenderoth, Lind & Ponack, L.L.P.

(57) ABSTRACT

One aspect of the apparatus comprising, a sensor configured to acquire a biological signal of a user, and a controller configured to, determine whether the biological signal is continuously outside a predetermined range for a first time period, after determining that the biological signal has been continuously outside the predetermined range for the first time period, then determine whether the biological signal is inside the predetermined range, and activate an alarm if the controller has determined that (i) the biological signal has been outside the predetermined range for the first time period, and (ii) the biological signal has been continuously inside the predetermined range for a second time period, the second time period being longer than the first time period.

13 Claims, 18 Drawing Sheets

(51) Int. Cl.

| | | |
|---|---|---|
| *G08B 25/08* | (2006.01) | |
| *A61B 5/0205* | (2006.01) | |
| *G08B 21/04* | (2006.01) | |
| *G08B 31/00* | (2006.01) | |
| *A61B 5/024* | (2006.01) | |
| *A61B 5/0245* | (2006.01) | |
| *A61B 5/113* | (2006.01) | |
| *A61B 5/08* | (2006.01) | |
| *G08B 21/02* | (2006.01) | |
| *G16H 40/67* | (2018.01) | |
| *G16H 50/20* | (2018.01) | |

(52) U.S. Cl.
CPC .............. *A61B 5/11* (2013.01); *A61B 5/6892* (2013.01); *A61B 5/7275* (2013.01); *A61B 5/746* (2013.01); *G08B 21/02* (2013.01); *G08B 21/04* (2013.01); *G08B 21/043* (2013.01); *G08B 21/0415* (2013.01); *G08B 21/0446* (2013.01); *G08B 21/0453* (2013.01); *G08B 21/0461* (2013.01); *G08B 25/08* (2013.01); *G08B 31/00* (2013.01); *G16H 40/67* (2018.01); *G16H 50/20* (2018.01); *A61B 5/02438* (2013.01); *A61B 5/02455* (2013.01); *A61B 5/1102* (2013.01); *A61B 5/113* (2013.01); *A61B 5/1118* (2013.01); *A61B 5/4809* (2013.01); *A61B 5/4812* (2013.01)

(56) References Cited

U.S. PATENT DOCUMENTS

| | | | | |
|---|---|---|---|---|
| 6,208,897 | B1* | 3/2001 | Jorgenson | A61N 1/3904 607/5 |
| 6,553,256 | B1* | 4/2003 | Jorgenson | A61B 5/00 128/898 |
| 7,834,770 | B2* | 11/2010 | Kazuno | G08B 21/0461 340/573.4 |
| 9,962,509 | B2* | 5/2018 | Landwehr | A61M 16/021 |
| 2002/0169583 | A1* | 11/2002 | Gutta | G08B 21/0453 702/188 |
| 2003/0050566 | A1* | 3/2003 | Ujhelyi | A61N 1/37258 600/515 |
| 2004/0147969 | A1* | 7/2004 | Mann | G16H 20/30 607/17 |
| 2005/0010254 | A1* | 1/2005 | Zhang | A61B 5/0402 607/9 |
| 2005/0054941 | A1* | 3/2005 | Ting | A61B 5/0408 600/529 |
| 2006/0258921 | A1* | 11/2006 | Addison | A61B 5/6829 600/323 |
| 2006/0267780 | A1* | 11/2006 | Adams | G08B 21/0423 340/573.1 |
| 2007/0013511 | A1* | 1/2007 | Weiner | G08B 21/0453 340/539.12 |
| 2007/0032733 | A1* | 2/2007 | Burton | A61B 5/4812 600/509 |
| 2009/0143692 | A1* | 6/2009 | Brockway | A61B 5/0452 600/516 |
| 2009/0281838 | A1* | 11/2009 | Lynn | G16H 50/70 705/3 |
| 2010/0286546 | A1* | 11/2010 | Tobola | A61B 5/1135 600/534 |
| 2011/0046498 | A1* | 2/2011 | Klap | A61B 5/7275 600/534 |
| 2011/0068929 | A1* | 3/2011 | Franz | A61B 5/746 340/573.1 |
| 2011/0112442 | A1* | 5/2011 | Meger | A61B 5/4094 600/595 |
| 2012/0053424 | A1* | 3/2012 | Kenalty | G01L 19/0092 600/300 |
| 2012/0190969 | A1* | 7/2012 | Kameli | A61N 1/3706 600/424 |
| 2012/0191151 | A1* | 7/2012 | Kameli | A61N 1/37512 607/6 |
| 2012/0191152 | A1* | 7/2012 | Kameli | A61N 1/375 607/7 |
| 2012/0203076 | A1* | 8/2012 | Fatta | A61B 5/681 600/300 |
| 2012/0271372 | A1* | 10/2012 | Osorio | A61B 5/7275 607/17 |
| 2012/0295510 | A1* | 11/2012 | Boeckle | A61B 5/0002 446/72 |
| 2012/0314901 | A1* | 12/2012 | Hanson | G06T 7/73 382/103 |
| 2013/0241728 | A1* | 9/2013 | Spector | G08B 21/0492 340/539.12 |
| 2014/0114142 | A1* | 4/2014 | Shaoulian | A61N 1/37247 600/301 |
| 2014/0253324 | A1* | 9/2014 | Tamez | G08B 21/0461 340/539.12 |
| 2014/0313913 | A1* | 10/2014 | Patwari | A61B 5/6891 370/252 |
| 2015/0201850 | A1* | 7/2015 | Orron | A61B 5/02055 600/301 |
| 2015/0276925 | A1* | 10/2015 | Scholten | G01S 7/003 702/150 |
| 2016/0275776 | A1* | 9/2016 | Shen | G16H 50/20 |
| 2017/0164832 | A1* | 6/2017 | Kaib | A61B 5/1125 |
| 2018/0109740 | A1* | 4/2018 | Pickett | G08B 27/001 |
| 2018/0117299 | A1* | 5/2018 | Gustavson | A61B 5/0205 |
| 2018/0263562 | A1* | 9/2018 | Laplante-Levesque | A61B 5/01 |
| 2018/0315285 | A1* | 11/2018 | Janssen | G08B 21/0453 |
| 2019/0150798 | A1* | 5/2019 | Glazer | A61B 5/0064 |
| 2019/0209084 | A1* | 7/2019 | Bryant | A61B 5/0464 |
| 2020/0090485 | A1* | 3/2020 | Casse | A61B 5/4818 |
| 2020/0353239 | A1* | 11/2020 | Daniels | A61B 5/0492 |

OTHER PUBLICATIONS

Kogure, T et al., "Automatic Sleep/Wake Scoring from Body Motion in Bed: Validation of a Newly Developed Sensor Placed under a Mattress" Journal of Physiological Anthropology, 2011, vol. 30, pp. 103-109.

Kogure, T et al., "Validation of a sheet-shaped body vibrometer for screening of obstructive sleep apnea", Drug Discoveries & Therapeutics, 2017, vol. 11, Issue 3, pp. 126-132.

* cited by examiner

ABNORMALITY DETERMINATION APPARATUS AND NON-TRANSITORY COMPUTER READABLE MEDIUM STORING PROGRAM

CROSS-REFERENCE TO RELATED APPLICATIONS

This application is based upon and claims the benefit of priority from Japanese Patent Application No. 2017-231224, filed Nov. 30, 2017, the entire contents of which are incorporated herein by reference.

FIELD

The present embodiment relates to an abnormality determination apparatus and a non-transitory computer readable medium storing a program.

BACKGROUND

Conventionally, an apparatus and a system which determine an abnormality of a patient and issue an alert have been known.

DETAILED DESCRIPTION

Figure 1:
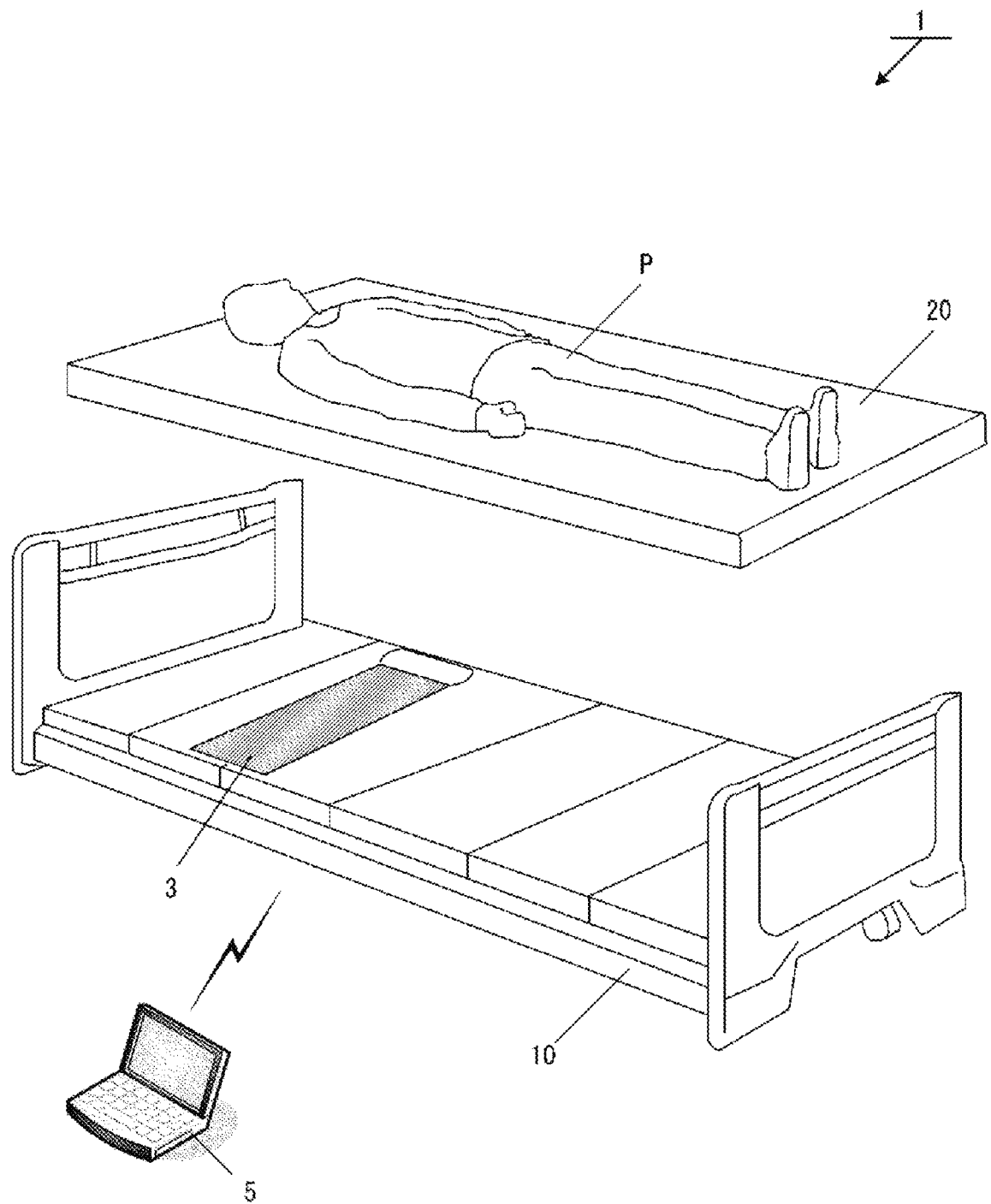
FIG. 1 is a diagram for explaining the whole system in a first embodiment.

One or more embodiments are now described with reference to the drawings, wherein like reference numerals are used to refer to like elements throughout. In the following description, for purposes of explanation, numerous specific details are set forth in order to provide a thorough understanding of the various embodiments. It is evident, however, that the various embodiments can be practiced without these specific details (and without applying to any particular networked environment or standard).

As used in this disclosure, in some embodiments, the terms "component," "system" and the like are intended to refer to, or comprise, a computer-related entity or an entity related to an operational apparatus with one or more specific functionalities, wherein the entity can be either hardware, a combination of hardware and software, software, or software in execution. As an example, a component may be, but is not limited to being, a process running on a processor, a processor, an object, an executable, a thread of execution, computer-executable instructions, a program, and/or a computer. By way of illustration and not limitation, both an application running on a server and the server can be a component.

One or more components may reside within a process and/or thread of execution and a component may be localized on one computer and/or distributed between two or more computers. In addition, these components can execute from various computer readable media having various data structures stored thereon. The components may communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software application or firmware application executed by a processor, wherein the processor can be internal or external to the apparatus and executes at least a part of the software or firmware application. As yet another example, a component can be an apparatus that provides specific functionality through electronic components without mechanical parts, the electronic components can comprise a processor therein to execute software or firmware that confers at least in part the functionality of the electronic components.

While various components have been illustrated as separate components, it will be appreciated that multiple components can be implemented as a single component, or a single component can be implemented as multiple components, without departing from example embodiments.

Further, the various embodiments can be implemented as a method, apparatus or article of manufacture using standard programming and/or engineering techniques to produce software, firmware, hardware or any combination thereof to control a computer to implement the disclosed subject matter. The term "article of manufacture" as used herein is intended to encompass a computer program accessible from any computer-readable (or machine-readable) device or computer-readable (or machine-readable) storage/communications media. For example, computer readable storage media can comprise, but are not limited to, magnetic storage devices (e.g., hard disk, floppy disk, magnetic strips), optical disks (e.g., compact disk (CD), digital versatile disk (DVD)), smart cards, and flash memory devices (e.g., card, stick, key drive). Of course, those skilled in the art will recognize many modifications can be made to this configuration without departing from the scope or spirit of the various embodiments.

In addition, the words "example" and "exemplary" are used herein to mean serving as an instance or illustration. Any embodiment or design described herein as "example" or "exemplary" is not necessarily to be construed as preferred or advantageous over other embodiments or designs. Rather, use of the word example or exemplary is intended to present concepts in a concrete fashion. As used in this application, the term "or" is intended to mean an inclusive "or" rather than an exclusive "or". That is, unless specified otherwise or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Embodiments described herein can be exploited in substantially any wireless communication technology, comprising, but not limited to, wireless fidelity (Wi-Fi), global system for mobile communications (GSM), universal mobile telecommunications system (UMTS), worldwide interoperability for microwave access (WiMAX), enhanced general packet radio service (enhanced GPRS), third generation partnership project (3GPP) long term evolution (LTE), third generation partnership project 2 (3GPP2) ultra mobile broadband (UMB), high speed packet access (HSPA), Z-Wave, Zigbee and other 802.XX wireless technologies and/or legacy telecommunication technologies.

In comparative example, if a biological information value such as a heart rate and a respiration rate shows an abnormality, a notification of abnormal change of a patient is made by issuing an alert.

In this case, there is a trouble that, for example, if the biological information value falls within a normal range after abnormality, it is determined that the patient is recovering, and a notification cannot be made in the case where a condition of the patient becomes further worse thereafter.

In particular, there is a trouble that, in the case where the patient comes close to death as a result of continuation of the abnormality of the patient, the biological information value does not always show an abnormal value, which results in failing to appropriately make a notification.

In general, according to one embodiment, one aspect of the apparatus comprising, a sensor configured to acquire a biological signal of a user, and a controller configured to, determine whether the biological signal is continuously outside a predetermined range for a first time period, after determining that the biological signal has been continuously outside the predetermined range for the first time period, then determine whether the biological signal is inside the predetermined range, and activate an alarm if the controller has determined that (i) the biological signal has been outside the predetermined range for the first time period, and (ii) the biological signal has been continuously inside the predetermined range for a second time period, the second time period being longer than the first time period.

In preferred embodiments, the sensor is further configured to sense an activity amount of the user, and the controller determines that the user comes close to death based on the biological signal and the activity amount.

In preferred embodiments, the controller determines that the user comes close to death when the controller has determined that (i) the biological signal has been outside the predetermined range for the first time period, (ii) the biological signal has been continuously inside the predetermined range for the second time period, and (iii) the activity amount is low during the second time period.

In preferred embodiments, the controller is configured to determine whether the user is out of bed based on the activity amount and to determine that the user comes close to death when the controller has determined that (i) the biological signal has been outside the predetermined range for the first time period, (ii) the biological signal has been continuously inside the predetermined range for the second time period, (iii) the activity amount is low during the second time period and (iv) the user is not out of bed.

In preferred embodiments, the controller is configured to determine a biological information value from the biological signal.

In preferred embodiments, the controller is configured to determine a heart rate and a respiration rate of the user as the biological information value.

In preferred embodiments, the sensor acquires the biological signal without contacting the user.

One aspect of the method comprising, acquiring with a sensor a biological signal of a user, and with a controller, determining whether the biological signal is continuously outside a predetermined range for a first time period, after determining that the biological signal has been continuously outside the predetermined range for the first time period, then determining whether the biological signal is inside the predetermined range, and activating an alarm if it has been determined that (i) the biological signal has been outside the predetermined range for the first time period, and (ii) the biological signal has been continuously inside the predetermined range for a second time period, the second time period being longer than the first time period.

In preferred embodiments, the method further comprising, sensing with the sensor an activity amount of the user, and determining with the controller that the user comes close to death based on the biological signal and the activity amount.

In preferred embodiments, the method comprising, determining that the user comes close to death when it determined that (i) the biological signal has been outside the predetermined range for the first time period, (ii) the biological signal has been continuously inside the predetermined range for the second time period, and (iii) the activity amount is low during the second time period.

In preferred embodiments, the method further comprising, determining with the controller whether the user is out of bed based on the activity amount, and determining that the user comes close to death when it is determined that (i) the biological signal has been outside the predetermined range for the first time period, (ii) the biological signal has been continuously inside the predetermined range for the second time period, (iii) the activity amount is low during the second time period and (iv) the user is not out of bed.

In preferred embodiments, the method further comprising, determining with the controller a biological information value from the biological signal.

In preferred embodiments, the method further comprising, determining with the controller a heart rate and a respiration rate of the user as the biological information value.

In preferred embodiments, the method comprising, the acquiring of the biological signal is done without the sensor contacting the user.

One aspect of the non-transitory computer readable medium having stored thereon a program for causing a microprocessor to execute at least the following, acquiring with a sensor a biological signal of a user, determining whether the biological signal is continuously outside a predetermined range for a first time period, after determining that the biological signal has been continuously outside the predetermined range for the first time period, then determining whether the biological signal is inside the predetermined range, and activating an alarm if it has been determined that (i) the biological signal has been outside the predetermined range for the first time period, and (ii) the biological signal has been continuously inside the predetermined range for a second time period, the second time period being longer than the first time period.

In view of the above-described aspects, the present embodiment provides an abnormality determination apparatus which is capable of appropriately determining an abnormal state of a patient on the basis of acquired biological information, and a non-transitory computer readable medium storing a program.

Embodiments for implementing the present invention will be described below with reference to the drawings. While some cases where abnormality determination apparatuses according to embodiments are applied are specifically described, the present invention is not limited to the embodiments described in these embodiments.

1. First Embodiment 1.1. Whole System

FIG. 1 shows an abnormality determination system 1 including the abnormality determination apparatus of a first embodiment. As illustrated in FIG. 1, the abnormality determination system 1 includes a detection apparatus 3 placed between sections a bed 10 and a mattress 20, and a processing apparatus 5 for processing a value output from the detection apparatus 3. The detection apparatus 3 and the processing apparatus 5 constitute the abnormality determination system (abnormality determination apparatus) for example. The bed 10 includes a base flame which place on a floor, a support flame which the base flame supports, a plurality of sections which the support flame supports, and at least one of drivers to drive the support flame and the sections. The sections including a back section, an upper leg section, a lower leg section, and a head section. Each section can move in accordance with the driver. The mattress 20 will place on the sections.

If a user (hereinafter, referred to as a "patient P" as an example) lies down on the mattress 20, the detection apparatus 3 detects body vibration (vibration produced from a human body) as a biological signal of the patient P. The detail method to detect body vibration is disclosed in Japanese patent application No. 2002-327624 (a title of this application: an input-output detector whether the patient is in-bed or not, filing date: Nov. 11, 2011) and in Journal of Japanese Society of Sleep Research whose title is "Sleep evaluation by a newly developed PVDF sensor non-contact sheet: a comparison with standard polysomnography and wrist actigraphy" written by Sunao UCHIDA, Takuro ENDO, Kazue SUENAGA, Hideto IWAMI, Shinsuke INOUE, Eiji FUJIOKA, Ayako IMAMURA, Takafumi ATSUMI, Yoshitaka INAGAKI and Atsushi KAMEI, published in 2011. The entire contents of the patent application and the journal are incorporated by reference.

Then, the processing apparatus 5 calculates a biological information value of the patient P on the basis of the vibration detected by the detection apparatus 3. In the present embodiment, the calculated biological information value (at least a respiration rate, a heart rate and an amount of activity) is displayed on the processing apparatus 5 as the biological information value of the patient P. However, a storage unit, a display unit, and processor, or the like, can be provided on the detection apparatus 3, such that the system may be integrally formed. Further, since the processing apparatus 5 may be a general-purpose processing apparatus, the processing apparatus 5 is not limited to an information processing apparatus such as a computer and may be configured with an apparatus such as, for example, a tablet or a smartphone.

Further, the patient may be an ailing person or a person who needs care. Further, the patient may be a healthy person who does not need care, an elderly person, a child, a disabled person or an animal.

Here, the detection apparatus 3 has a sheet shape so as to be thin. Therefore, even if the detection apparatus 3 is placed between the bed 10 (the sections of the bed) and the mattress 20, since the detection apparatus 3 can be used without providing a feeling of strangeness to the patient P, it is possible to measure a biological information value in bed for a long period. That is, a biological information value is acquired as a state of the patient when the patient is lying on the bed, is in a resting state, or is at rest.

Note that the detection apparatus 3 only has to be able to acquire a biological signal (such as body motion, respiratory movement and ballistocardiogram) of the patient P. The processing apparatus calculates a heart rate and a respiration rate on the basis of body vibration. Alternatively, the detection apparatus 3 can be configured to include an infrared sensor, a video camera, or an actuator with a strain gauge to acquire a biological signal of the patient. Further, the detection apparatus 3 may be implemented by, for example, a smartphone placed on the bed 10 with use of a built-in acceleration sensor, a tablet, placed on the bed 10 with use of a built-in acceleration sensor, or the like.

1.2. Configuration of the System

Figure 2:
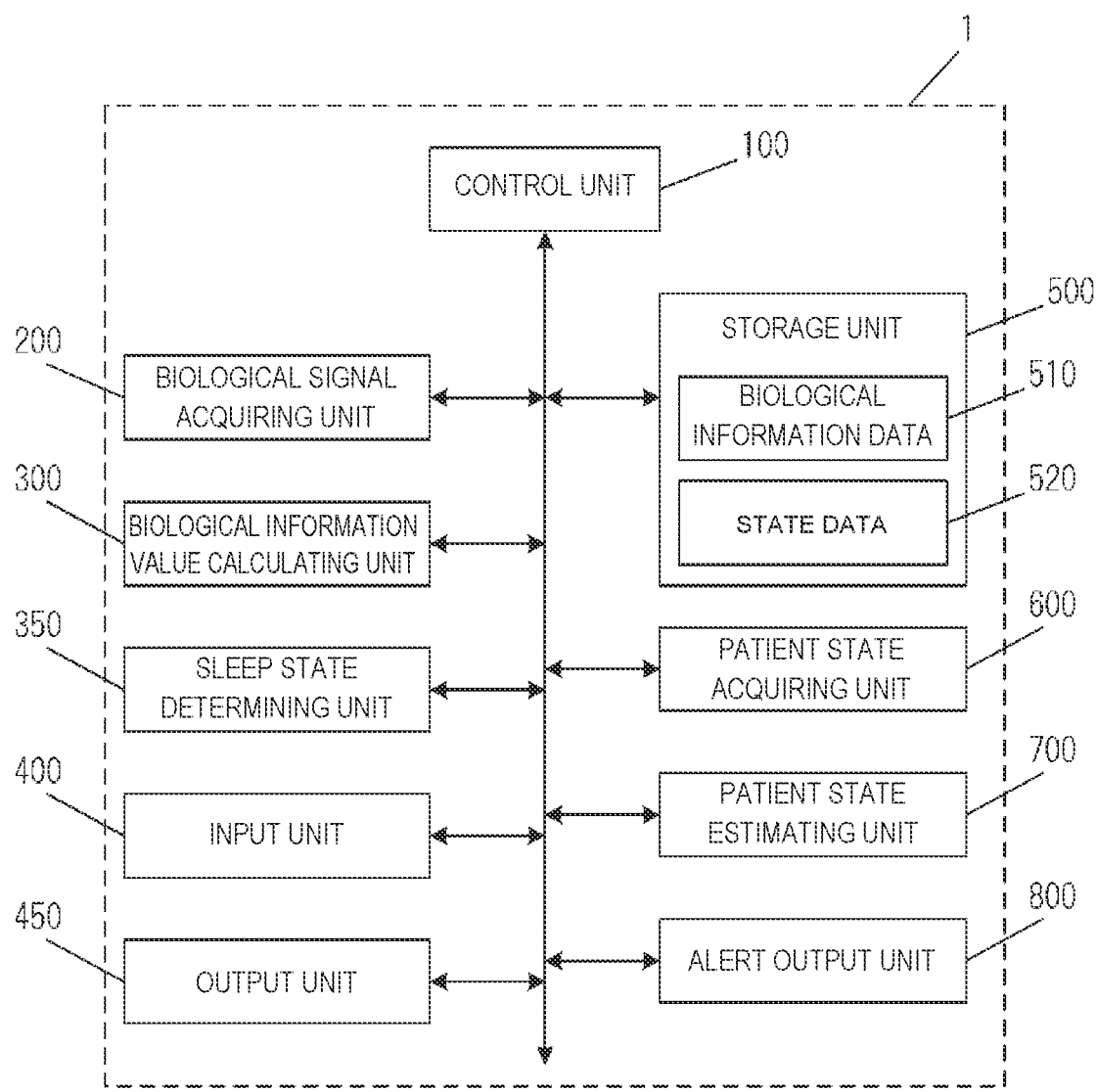
FIG. 2 is a diagram for explaining a configuration of the system or apparatus in the first embodiment.

Subsequently, a configuration of the abnormality determination system 1 will be described using FIG. 2. The system 1 in the present embodiment includes the detection apparatus 3 and the processing apparatus 5. Although the system 1 includes a plurality of units in FIG. 2, all unit (processing) other than the biological signal acquiring unit 200 may be implemented by either one of the apparatuses. That is, the units including inputs such as detected or sensed information, outputs, and processing, described herein are implemented in hardware, such as detectors, sensors, microprocessors, input/output devices, displays, speakers, and software stored on electronic non-transitory memory, and such hardware can be physically included in either the processing device 5, or the sensor 3, or distributed between the processing device 5 or the sensor 3.

The system 1 (abnormality determination apparatus) includes a control unit 100, a biological signal acquiring unit 200, a biological information value calculating unit 300, a sleep state determining unit 350, an input unit 400, an output unit 450, a storage unit 500, a patient state acquiring unit 600, a patient state estimating unit 700 and an alert output unit 800. The control unit 100, the biological signal acquiring unit 200 and the storage unit 500 can be provided at the detection apparatus 3, while the other units are provided at the processing apparatus 5. Further, the biological signal acquiring unit 200 may be utilized as the patient state acquiring unit 600, or the patient state acquiring unit 600 may be separately provided on the bed 10 against the biological signal acquiring unit 200.

The system 1 performs alerting (notification) operation after determining that a state of the patient is an abnormal state. If the system 1 determines the state of the patient is an abnormal state, a processing apparatus sends or activates an alert via an alert output unit 800, in a manner that can be noticed by caregivers like a staff or a family member. The output unit 800 can be configured to include a sound generator and speaker to outputs or activates the alert (notification) or can issue or activates the alert on a screen display or may output or activates the alert as an electronic indication to a mobile terminal apparatus or other terminal apparatuses, or the like, through an e-mail, or the like.

The control unit 100 controls entire operations of the system 1 (the abnormality determination system 1). The control unit 100 may be configured with, for example a control apparatus such as a microprocessor, a CPU, or a computer. The control unit 100 performs processing by reading out and executing programs stored in the storage unit (electronic memory) 500. Note that, while, in the present embodiment, the control unit 100 operates for the whole system, the control unit 100 may be respectively provided at the detection apparatus 3 and the processing apparatus 5. In other words, the control unit can be implemented for the whole system by a microprocessor in either the processing apparatus 5 or the detection apparatus 3, or the control unit can be implemented by separate microprocessors handling respective functions in the processing apparatus 5 and the detection apparatus 3.

The biological signal acquiring unit 200 acquires a biological signal of the patient P. The biological signal acquiring unit 200 can include a pressure change sensor that detects body vibration, which is one type of the biological signal. The biological information value calculating unit 300 converts the acquired body vibration into biological information value data such as a respiration rate, a heart rate and an amount of activity and outputs the biological information value data. Further, the biological information value calculating unit 300 can determine a state of the patient (for example, whether or not the patient P is lying down in the bed, whether the patient P gets out of the bed, postures the patient is staying in the bed, positions the patient is staying in the bed, or the like) on the basis of body vibration data or determine a state of the patient (whether the patient is sleeping or awaken) as will be described later.

The detail method to determine the state of the patient which related to whether the patient is sleeping or awake is disclosed in Journal of Physiological Anthropology whose title is "Automatic Sleep/Wake Scoring from Body Motion in Bed: Validation of a Newly Developed Sensor Placed under a Mattress" written by Takamasa Kogure, Shuichiro Shirakawa, Masato Shimokawa and Yuji Hosokawa, published in 2011. The entire contents of the journal are incorporated by reference.

The biological signal acquiring unit 200 calculates the reference D disclosed in the above journal and determines whether the patient is sleeping or awake based on comparison the reference with the threshold number 1.

Note that, while the biological signal acquiring unit 200 in the present embodiment, for example, acquires body vibration of the patient with a pressure sensor and acquires respiration and heartbeat from the body vibration, the biological signal acquiring unit 200 may acquire a biological signal from change in a position of the center of gravity (body motion) of the patient with a load sensor, may acquire a biological signal on the basis of motion of a body surface or bedclothes with a radar or may acquire a biological signal on the basis of sound picked up with a microphone by the microphone being provided. It is only necessary that a biological signal of the patient can be acquired using one of the sensors.

The detail method how to detect the change of the position of the center of the gravity is disclosed in Japanese patent application No. 2002-327633 (a title of this application: a detector where the patient is on the bed, filing date: Nov. 11, 2011). The entire contents of the patent application are incorporated by reference.

That is, the biological signal acquiring unit 110 may be provided in an apparatus such as the detection apparatus 3, an apparatus such as the detection apparatus 3 may be connected to the biological signal acquiring unit 200, or the biological signal acquiring unit 200 may be configured to receive a biological signal from external apparatuses.

The biological information value calculating unit 300 calculates a biological information value (such as a respiration rate, a heart rate and an amount of activity) of the patient P. In the present embodiment, it is also possible to extract a respiratory component and a heartbeat component from the body motion acquired by the biological signal acquiring unit 200 and obtain a respiration rate and a heart rate on the basis of a respiratory interval and an R-R interval. The R-R interval indicates an interval from a peak point of an R wave to the next peak point of the R wave in an electrocardiogram. Further, it is also possible to analyze (perform Fourier transform, or the like, on) periodicity of the body motion and calculate a respiration rate and a heart rate from a peak frequency.

Further, it is also possible to detect body vibration per predetermined time period from the biological signal acquiring unit 200 and calculate the number of times of the detected body vibration as an amount of activity.

The sleep state determining unit 350 determines a state of the patient which related to whether the patient is sleeping or awake. For example, the state of the patient is determined on the basis of the biological signal acquired by the biological information value calculating unit 300. As the state of the patient, the state of the patient may include "waking" (the state the patient is waking) or "sleeping" (the state the patient is sleeping), or further, may include "REM sleep" (the state the patient is sleeping and a level of sleeping is REM) or "non-REM sleep" (the state the patient is sleeping and a level of sleeping is non-REM), or may include a depth level of sleeping.

The input unit 400 utilized when caregivers or doctors input various conditions or perform operation input to start measurement. For example, the input unit 400 is implemented by any input means such as a hardware key and a software key.

The output unit 450 is utilized when the biological information value such as the state of the patient ("sleeping", "waking", or the like), the heart rate and the respiration rate is output, or when a notification of an abnormality is made. The output unit 450 may be a display apparatus such as a display or a notification apparatus (sound output apparatus) which makes a notification of an alarm, activates the alarm, or the like. Further, the output unit 450 may be an external storage apparatus which stores data, a transmission apparatus which transmits data through a communication path, or the like. Still further, the output unit 450 may be a communication apparatus in the case where an alert is issued or activated to other apparatuses.

The storage unit 500 stores various kinds of data and programs for operation of the abnormality determination system 1. The control unit 100 implements various kinds of functions by reading out and executing the programs stored in the storage unit 500. The storage unit 500 is configured with, for example, a semiconductor memory, a magnetic disk apparatus, or the like. Biological information data 510 is stored in the storage unit 500.

In the biological information data 510, a respiration rate and a heart rate obtained from the acquired biological signal (body motion) are stored. Note that, while, in the present embodiment, the respiration rate, the heart rate and the body motion are stored, it is necessary that at least one of them is stored. Further, other information (for example, a respiratory event index based on fluctuation, or the like, of a respiratory amplitude, a periodic body motion index based on periodicity of body motion) may be further stored if the information is the biological information value which can be calculated by the biological information value calculating unit 300.

In state data 520, a state of the patient related to whether the patient is sleeping or waking is stored. As the state of the patient determined by the sleep state determining unit 350, a state of the patient such as whether the patient is "sleeping" or "waking", or a state of the patient such as whether the patient is staying in the bed (that is, "in-bed") or gets out of the bed ("out-of-bed") acquired by the patient state acquiring unit 600 are stored.

The patient state acquiring unit 600 acquires a state of the patient. For example, a state of the patient (such as whether the patient is staying in the bed or gets out of the bed) is acquired with a load sensor, or the like, provided in the bed 10. Note that, as described above, the patient state acquiring unit 600 may be implemented in the biological signal acquiring unit 200.

The patient state estimating unit 700 estimates a state of the patient from a parameter such as a biological information value. If the state of the patient is estimated as abnormal by the patient state estimating unit 700, an alert is output (notified) or activated by the alert output unit 800. Note that the patient state estimating unit 700 may estimate that an abnormality of the patient continues.

Further, in the present embodiment, the patient state estimating unit 700 can determine (estimate) that whether an abnormal state of the patient continues. That is, if the abnormal state of the patient continues, the patient state estimating unit 700, for example, estimates, notifies, and activates that the patient comes close to death (is dying).

A state where the patient comes close to death refers to a state where the end of the life of the patient approaches. That is, the state where the end of the life of the patient indicates the patient will die within a predetermined time period from a timing where the patient state estimating unit 700 recognizes the abnormal state of the patient.

As one criterion, for example, a timing at which the patient dies within a predetermined time period (for example, 3 hours, 6 hours, 12 hours, 24 hours) is referred to as a state where the patient comes close to death. In the present embodiment, while a period from approximately 12 to 24 hours is assumed as the predetermined time period, the predetermined time period is changed by setting of parameters.

Further, a method in which the state of the patient is estimated as an abnormal state by the patient state estimating unit 700 according to the present embodiment will be described.

Figure 3:
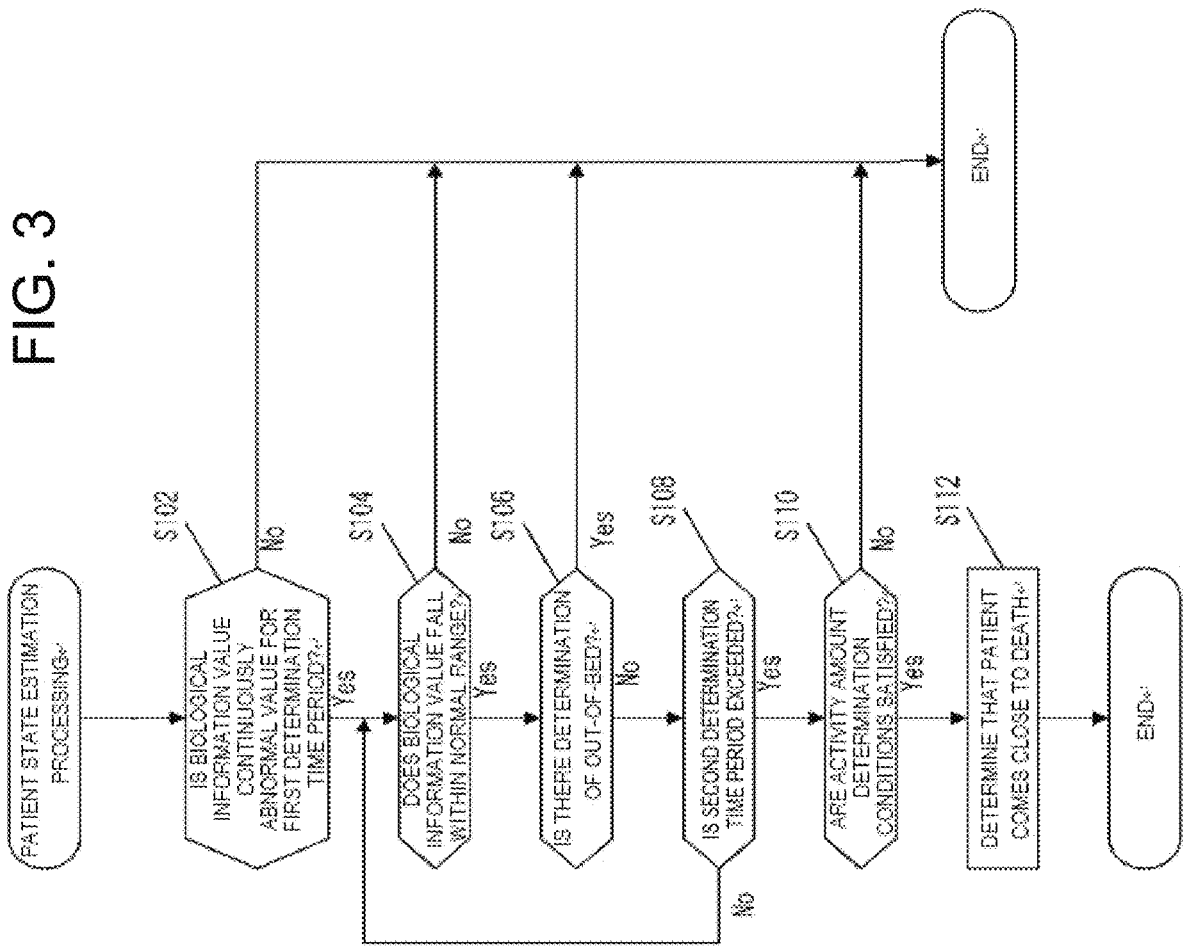
FIG. 3 is an operation flow for explaining patient estimation processing in the first embodiment.

FIG. 3 is an algorithm or a processing flow of the patient state estimation processing. The algorithm or the processing flow shown in FIG. 3 is stored as a program in a memory (as the storage unit 500) and executed by a microprocessor (as the control unit 100).

In the patient state estimation processing shown in FIG. 3, the biological information value calculating unit 300 calculates the biological information value of the patient, and the sleep state determining unit 350 determines the state of the patient related to whether the patient is sleeping or waking.

The sleep state determining unit 350 and the patient state acquiring unit 600 determine the state of the patient such as whether the patient is "sleeping" or "waking", or a state of the patient such as whether the patient is staying in the bed or gets out of the bed and the patient state estimating unit 700 estimates the state of the patient in detail while, in executing the process shown in FIG. 3, changes of quality of sleeping, changes as to whether the patient can sleep well during midnight for example, increase of a time period in which the patient is staying in bed, increase of a time period in which the patient is not in bed, a continuous time period in which the patient is staying in bed, a continuous time period in which the patient is not in bed, or the like, are taken into account by the patient state estimating unit 700.

Further, the biological information value calculating unit 300 acquires a respiratory problem index and a periodic body motion index, which are indexes (biological indexes) as one of the biological information values of the patient, and the patient state estimating unit 700 estimates the state of the patient in more detail from absolute values of these indexes, daily change of an average value, and change of time-series distribution of 24 hours. Further, through the memory, the biological information value calculating unit 300 acquires a history of the biological information value and a past value of the biological information value, and determines an average value, standard deviation, a variation coefficient, a value or a ratio of change in the latest predetermined time period.

The detail method how to calculate the respiratory problem index is disclosed in Journal of *Drug Discoveries & Therapeutics* whose title is "Validation of a sheet-shaped body vibrometer for screening of obstructive sleep apnea" written by Takamasa Kogure, Mina Kobayashi, Takashi Okawa, Tsuneya Nakajima, Yuichi Inoue, published in 2017. The entire contents of the journal are incorporated by reference.

The biological signal may be directly acquired as the biological information value or may be calculated by predetermined operation being executed from the biological signal. Further, other biological information values or indexes may be calculated from a plurality of biological information values or biological signals.

Subsequently, the patient state estimating unit 700 determines whether or not the biological information value continuously indicates an abnormal value for a first determination time period. For example, the first determination time period is preferably equal to or longer than 15 minutes, and, more preferably, equal to or longer than 30 minutes. That is, the patient state estimating unit 700 determines whether or not the biological information value indicates an abnormal value for a period exceeding the first determination time period. Further, in addition to the situation where the biological information value continuously indicates an abnormal value, the patient state estimating unit 700 also determines that the biological information value is abnormal if an average value of the biological information value during the first determination time period indicates an abnormal value, even though the biological information value falls within a normal range only for a short period of time (for example, approximately, several seconds).

Further, while, in the present embodiment, the respiration rate and the heart rate are utilized as the biological information values, other biological information values such as a blood pressure and oxygen saturation may be utilized. Further, one of the respiration rate and the heart rate may be utilized. Here, as an example of a normal range of each biological information value is, the respiration rate of 8 to 25 times/minute, and the heart rate of 50 to 110 times/minute, and if the value of the biological information value falls outside this range, the patient state estimating unit 700 treats the biological information values as an abnormal value. Note that this normal range may change in accordance with age, weight, or the like, of the patient. Further, a normal biological information value may be set as a normal range for each patient.

That is, the normal range is a range of the value which is indicated as the biological information value when the patient is normal, and may indicate a normal value (normal range).

As an example based on the above, when the respiration rate and the heart rate are abnormal for at least 30 minutes (first determination time period), and then become not abnormal, the patient state estimating unit 700 determines whether or not they remain not continuously abnormal for a second determination time period.

Specifically, when the respiration and heart rate are continuously abnormal for the second time period, or when the respiration and heart rate reach the abnormal state at least one time during the second time period (step S102: Yes→step S104: No), the patient state estimating unit 700 determines that the state of the patient is not a state in which the patient does not come close to death (a state in which the patient will die after the predetermined time period or a state in which the end of the life of the patient does not approach), or determines that the state of the patient is a state in which the patient is already dead. when the respiration and heart rate are continuously abnormal for the second time period, or when the respiration and heart rate reach the abnormal state at least one time during the second time period (step S102: Yes→step S104: No), the processing flow is completed. The patient state estimating unit 700 will repeatedly monitor whether the condition of the step S102 is satisfied after completing this processing flow.

Further, also if the patient gets out of the bed for equal to or longer than a certain time period during this second determination time period (step S106: No), the patient state estimating unit 700 determines that the state of the patient is not an abnormal state (the patient does not come close to death). Again the patient state estimating unit 700 will repeatedly monitor whether the condition of the step S102 is satisfied after completing this processing flow.

In this manner, if the patient state estimating unit 700 detects the biological information values (the respiration rate and the heart rate) fall or are within the normal ranges during the second determination time period, and if the patient state estimating unit 700 detects that the patient is always staying in the bed during this second determination time period (step S102: Yes→step S104: Yes), the patient state estimating unit 700 will execute a step S108.

Here, while the second determination time period is preferably equal to or longer than 12 hours, the second determination time period only has to be equal to or longer than 6 hours. Further, while it is described that the biological information values fall or are within the normal ranges, preferably, if the biological information values continuously fall or are within the normal ranges for the second determination time period, even if the biological information values fall or are within abnormal ranges for, for example, less than a predetermined time period (for example, one minute, or a period corresponding to several detection timings), the patient state estimating unit 700 may determine that the biological information values continuously fall within the normal ranges.

Then, if activity amount determination conditions are satisfied (step S108: Yes→step S110: Yes), the patient state estimating unit 700 determines that the patient comes close to death (step S112).

The activity amount determination conditions are conditions for determining whether or not the patient comes close to death in accordance with the amount of activity and motion of the patient. In the present embodiment, for example, if an average amount of activity of the patient during the second determination time period is equal to or less than 5 times/minute, or if a duration while there is no body motion exceeds 12 hours (preferably, 12 hours, but may be, for example, 6 hours), the patient state estimating unit 700 determines that the patient comes close to death. The amount of activity is calculated by the number where a amplitude of body vibration exceeds a predetermined threshold. Therefore the patient state estimating unit 700 counts the number where a amplitude of body vibration exceeds a predetermined threshold during one minute to execute the step S108.

In this manner, in a case where the patient comes close to death, there can be seen such characteristics and tendency that after the respiration rate and the heart rate no longer indicate abnormal values, there is little body motion over a long time period if the patient does not get out of the bed. The little body motion corresponds to the case the biological information values fall or are within the normal range, that is, the step S104.

If the amount of activity of the patient is relatively low corresponding to the little body motion, the patient state estimating unit 700 determines that the patient comes close to death. Whether or not the amount of activity of the patient is relatively low is determined by the above-described determination conditions or in accordance with whether or not the patient continues to sleep (the amount of activity is too low to be determined as sleeping).

Therefore, in the present embodiment, it is possible to discern whether the patient is recovering from a poor physical condition to a normal condition, or physical condition of the patient becomes further worse and the patient comes close to death based on the above described characteristics and tendency. By this means, it is possible to prevent a state where physical condition becomes further worse and the patient comes close to death from erroneously determined as a state where the patient is recovering from the poor physical condition to the normal condition.

Note that, while, in the above-described embodiment, the patient state acquiring unit 600 determines in step S106 whether or not the patient gets out of the bed, the determination may not be performed. That is, if the biological information value falls within the normal range for the second determination time period after the biological information value continuously indicates an abnormal value for the first determination time period, the patient state estimating unit 700 may determine whether or not the activity amount determination conditions are satisfied.

Further, in the case where the patient comes close to death, a respiratory event and periodic body motion prominently decrease. Therefore, the respiratory event and the periodic body motion are particularly useful in the case where body motion of a person other than the patient, such as nurses, caregivers and an attendant family member.

2. Second Embodiment

Subsequently, a second embodiment will be described in FIG. 4. In the first embodiment, an abnormal state of the patient, particularly, the state where the patient comes close to death is determined by determining the input biological information at the patient state estimating unit 700 on the basis of the biological information value, and at least one of "motion of the patient (the amount of activity)", "fluctuation in a respiratory amplitude (a respiratory event index)" and "periodic motion of the patient (a periodic body motion index)".

In the present embodiment, a case where the patient state estimating unit 700 estimates the state of the patient using artificial intelligence (machine learning) will be described by using FIG. 4.

Figure 4:
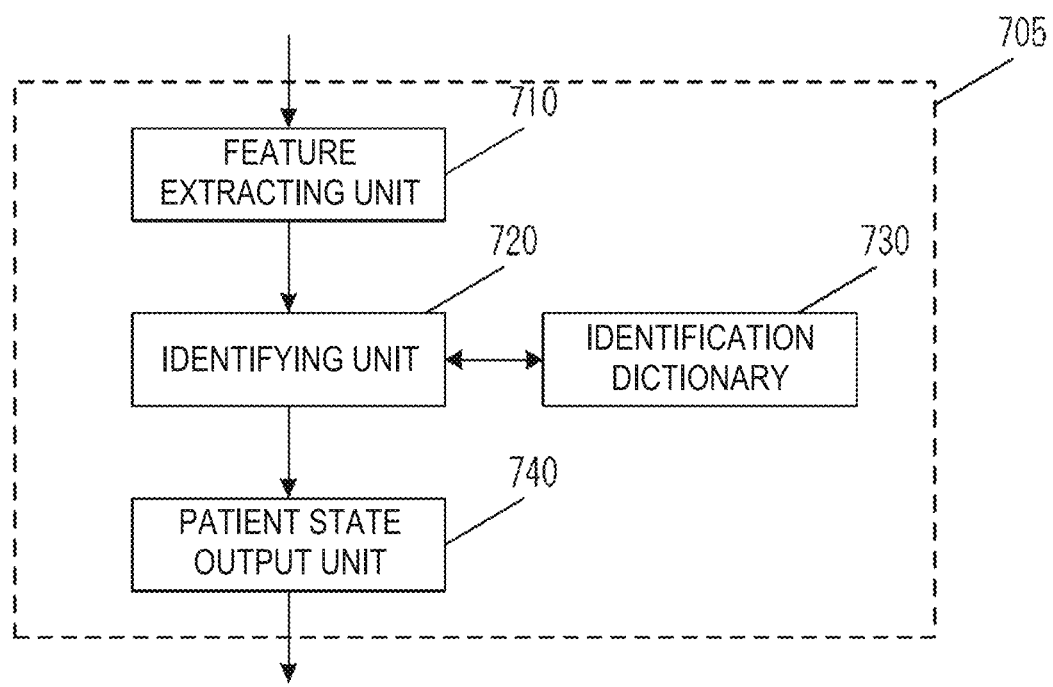
FIG. 4 is a diagram for explaining a configuration of a patient state estimating unit in a second embodiment.

In the present embodiment, the state of the patient is estimated on the basis of the patient state estimating unit 705 in FIG. 4.

Here, operation of the patient state estimating unit 705 in the present embodiment will be described. The patient state estimating unit 705 estimates the state of the patient by utilizing artificial intelligence and statistical indicators using the biological information and the state of the patient as input values (input data).

As illustrated in FIG. 4, the patient state estimating unit 705 includes a feature extracting unit 710, an identifying unit 720, an identification dictionary 730 and a patient state output unit 740.

First, as the input data to the patient state estimating unit 705, various parameters are input and utilized. For example, in the present embodiment, the "respiration rate", the "heart rate" and the "amount of activity" calculated by the biological information calculating unit on the basis of the body vibration data acquired by the biological signal acquiring unit 200, the "a state of the patient which related to whether the patient is sleeping or awake" determined by the sleep state determining unit 350, or the like, are utilized. It is also possible to utilize "variation in the respiration rate", "variation in the heart rate" calculated from these biological information values, and "a respiratory problem index" and "a periodic body motion index" calculated from the same body vibration data.

Here, the state of the patient includes states whether the patient is staying in the bed or not, whether the patient gets out of the bed or not, and whether the patient is sleeping or awake if the patient the patient is staying in the bed.

Then, each feature point is extracted by the feature extracting unit 710 and output as a feature vector. Here, for example, the following can be extracted as the feature points.

(1) the respiration rate of equal to or higher than 30 [times/minute] or equal to or lower than 8 [times/minute] continues for equal to or longer than a certain time period
(2) the heart rate of equal to or higher than 120 [times/minute] or equal to or lower than 40 [times/minute] continues for equal to or longer than a certain time period
(3) trend of the heart rate and the respiration rate increases (by equal to or greater than 10%) from start to end of night sleeping
(4) variation (standard deviation, a variation coefficient) in the respiration rate or the heart rate in night time (from 21:00 to 6:59) is equal to or greater than a certain value
(5) the respiratory problem index or the periodic body motion index significantly decreases
(6) the respiratory problem index or the periodic body motion index significantly increases or is equal to or greater than a certain value (night time)
(7) the amount of activity significantly increases or decreases
(8) sleeping continues for equal to or longer than a certain time period, and waking during the night time is equal to or higher than 95%

The feature vector is output by combining one or more of these feature points. Note that the above is an example of the feature points, and the feature points are not limited to the above values. In the example of (1), the respiration rate may be equal to or higher than 25 [times/minute], or may be equal to or lower than 10 [times/minute]. In this manner, each value is a value for convenience of description. The feature vector may be output as "1" if the patient is satisfied with one feature point, and the feature vector may be output as "0" if the patient is not satisfied with one feature point, or a random variable may be output.

Then, in the case where all the above-described feature points are included, feature vector space is eight dimensions, and an eight-dimensional feature vector is output to the identifying unit 720.

The identifying unit 720 identifies a class corresponding to the state of the patient from the input feature vector. At this time, the class is identified by checking against a plurality of prototypes prepared in advance as the identification dictionary 730. The prototypes may be stored as feature vectors corresponding to respective classes or a feature vector representing the class may be stored.

In the case where the feature vector representing the class is stored, a class to which the closest prototype belongs is determined. At this time, the class may be determined using a nearest neighbor rule or may be identified using k-nearest neighbor algorithm.

Note that, in the identification dictionary 730 utilized by the identifying unit 720, prototypes may be stored in advance or storage may be performed by utilizing machine learning.

Then, the state of the patient is output by the patient state output unit 740 in accordance with the class identified by the identifying unit 720. The state of the patient to be output is "normal" or "abnormal", and if the patient state estimating unit 705 determines the state of the patient as abnormal, the patient state estimating unit 705 may determine the state of the patient is a state where "the patient comes close to death", or determine the state of the patient is a state where the patient "has recovered", or the like, or a random variable may be output.

By this means, according to the present embodiment, it is possible to acquire biological information including the "respiration rate", the "heart rate", the "amount of activity", "whether the patient gets out of the bed or not," and "whether the patient is staying in the bed or not", and the patient state estimating unit 705 estimates whether or not the patient comes close to death from this biological information.

3. Third Embodiment

Figure 5:
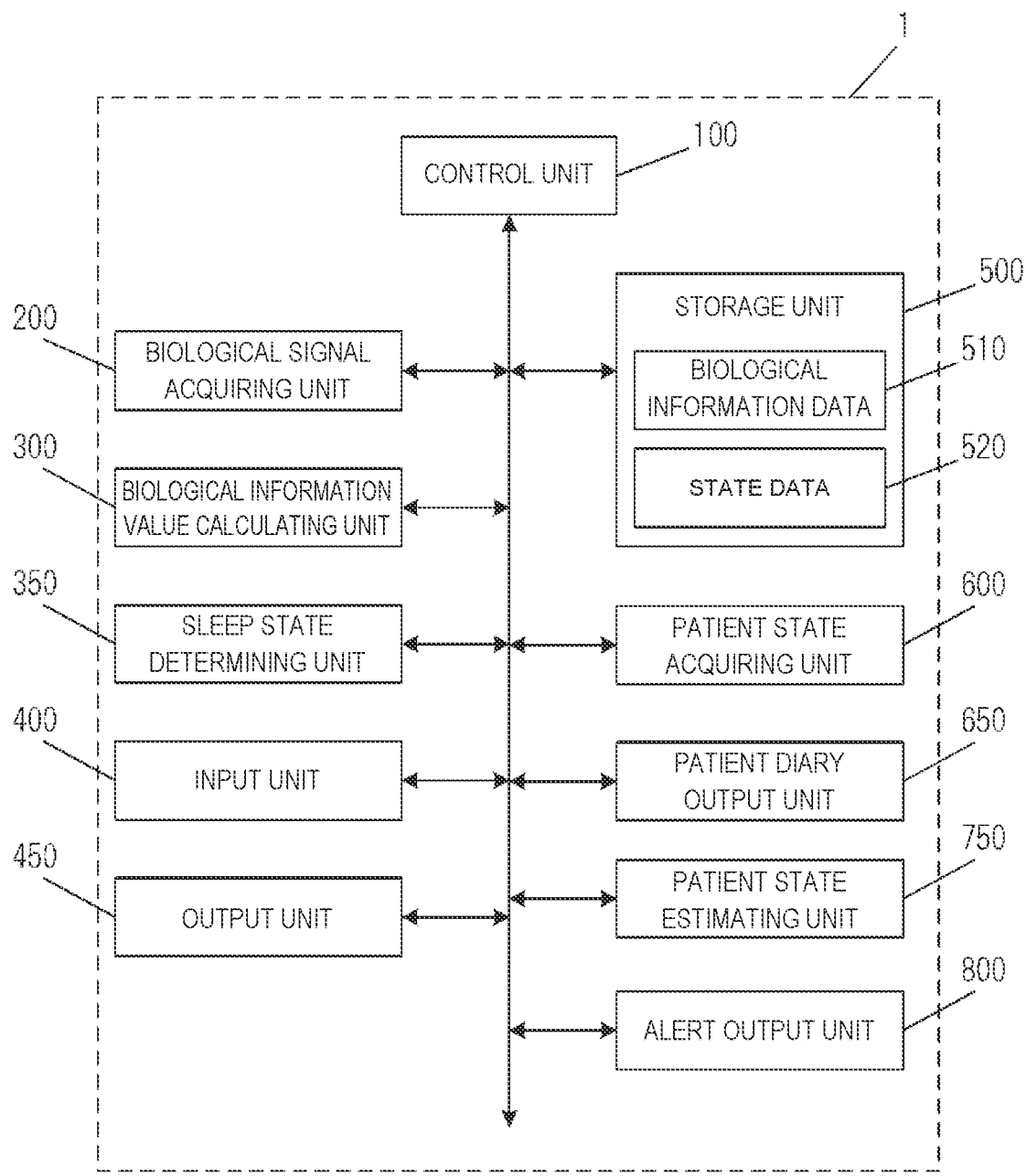
FIG. 5 is a diagram for explaining a configuration of the system or apparatus in a third embodiment.

Subsequently, the third embodiment will be described. The third embodiment is an embodiment in which a configuration in FIG. 2 of the first embodiment is replaced with that in FIG. 5.

In addition to the configuration of the first embodiment, the patient diary output unit 650 is further provided. Further, in place of the patient state estimating unit 700, a patient state estimating unit 750 which estimates the state of the patient by utilizing a neural network is provided.

The patient diary output unit 650 outputs the acquired biological information value and the state of the patient ("0" indicates "out-of-bed", "1" indicates "in-bed" and a state where the patient is waking, "2" indicates "in-bed" and a state where the patient is sleeping) as image data (image data of "pixels corresponding to 1440 pixels×days") in which one line is made to correspond to 24 hours and the data is expressed with a value of a pixel value for each minute. As the patient diary, a respiratory diary indicating the respiration rate of the patient, a heartbeat diary indicating the heart rate of the patient, a sleep diary indicating the state of the patient related to whether the patient is sleeping or waking, an activity amount diary indicating body motion of the patient, a respiratory problem diary indicating the number of times of a respiratory problem event, a periodic body motion diary indicating the number of times of a periodic body motion event, or the like, can be output. Note that it is also possible to output one patient diary in which these parameters are combined. It is possible to output graphs of these patient diaries as diary data which is image data.

Figure 6:
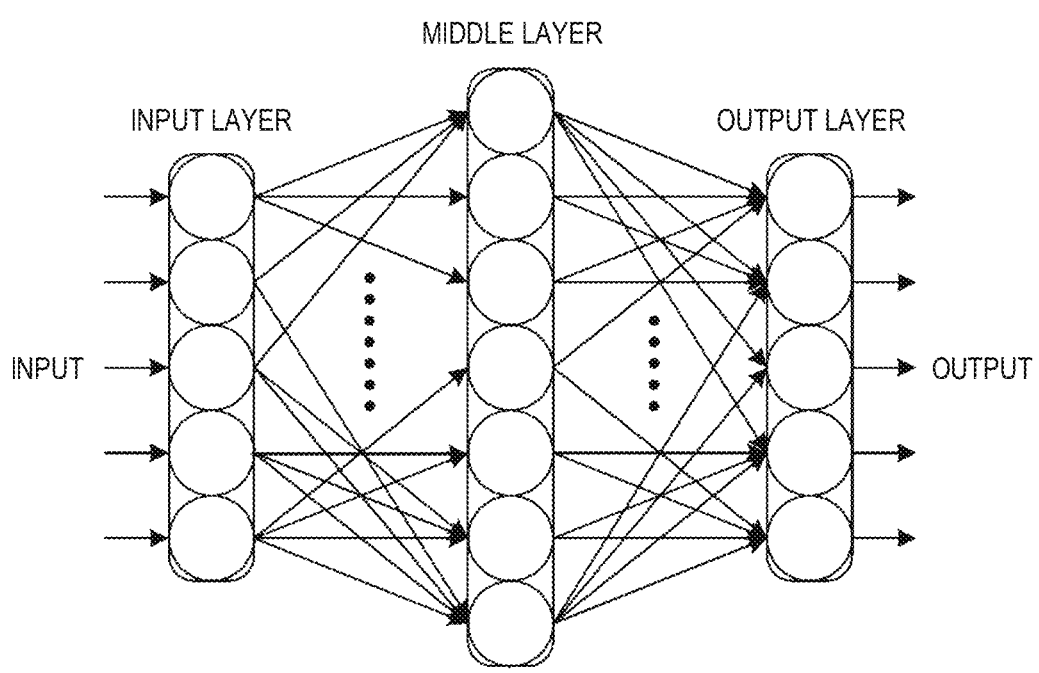
FIG. 6 is a diagram for explaining a neural network in the third embodiment.

The patient state estimating unit 750 estimates the state of the patient from the input diary data. Here, as processing of estimating the state of the patient, recently, particularly, deep learning (deep neural network) has high accuracy in image recognition, and this method is utilized as an example also in the present embodiment. Processing in the deep learning will be simply described using FIG. 6.

First, the patient state estimating unit 750 inputs signals of the diary data (image data) output from the patient diary output unit 650 to a neural network formed with a plurality of layers and neurons included in each layer. Each neuron receives signals from another plurality of neurons and outputs signals subjected to calculation to another plurality of neurons. In the case where the neural network has a multi-layered structure, layers are referred to as an input layer, a middle layer (hidden layer) and an output layer in order of signals flowing.

A neural network in which a middle layer of the neural network is formed with a plurality of layers is referred to as a deep neural network (for example, a convolutional neural network in which convolution operation is performed), and a method of machine learning using this is referred to as deep learning.

Neurons of each layer of the neural network of the diary data are subjected to various kinds of operation (such as convolution operation, pooling operation, normalization operation and matrix operation) and flow while forms are changed, and a plurality of signals are output from the output layer.

A plurality of output values from the neural network are respectively associated with states of the patient, and processing of estimating a state of the patient associated with the largest output value, or the like, is performed. Alternatively, even if the state of the patient is not directly output, the state of the patient may be estimated from output of a classifier by applying one or more output values to the classifier.

Parameters which are coefficients to be used for various kinds of operation of the neural network are determined by inputting a number of pieces of diary data and states of the patient of the diary data to the neural network in advance, propagating errors between the output values and a correct value in an inverse direction on the neural network using a backpropagation method, and updating parameters of neurons of each layer a number of times. In this manner, process of updating and determining parameters is referred to as learning.

A structure of the neural network and each operation are well-known technologies explained in books and papers, and it is only necessary to utilize one of the technologies.

By utilizing the patient state estimating unit 750, whether or not the patient comes close to death is output as the state of the patient from the input data such as the biological information of the patient.

Note that, while, in the above-described embodiment, the neural network is utilized by inputting diary data in which one line is made to correspond to 24 hours, it is also possible to utilize diary data in which one line is made to correspond to seven days in view of weekly rhythmic periodicity, diary data in which one line is made to correspond to 28 days in view of substantially monthly rhythmic periodicity, diary data in which one line is made to correspond to 365 days in view of yearly rhythmic periodicity, or the like, or utilize the neural network by inputting the biological information value without taking into account rhythmic periodicity in advance. That is, it is also possible to estimate the state of the patient by inputting information such as the "heart rate", the "respiration rate", the "amount of activity", "out-of-bed", "in-bed", the "number of times of a respiratory event", and the "number of times of periodic body motion" to the neural network in synchronization with respective time axes, and causing the neural network to learn.

4. Examples

An example where the state of the patient (the patient comes close to death) is determined by utilizing the above-described embodiments will be described. FIG. 7 to FIG. 18 are diagrams for explaining an example of the patient diary. Here, FIG. 7 to FIG. 9 and FIG. 10 to FIG. 12 are patient diaries in the case where the patient has recovered, and FIG. 13 to FIG. 15 and FIG. 16 to FIG. 18 are examples of the patient diaries in the case where the patient has died.

The present drawings are examples of the patient diaries in which the state of the patient related to whether the patient is sleeping or not is indicated for each day, and graphs indicating the state of the patient related to whether the patient is sleeping or not for each day in a vertical direction are illustrated.

In all the patient diaries, one line corresponds to 24 hours, and the center of the graph indicates midnight. Further, for example, as the biological information values, normal ranges of the respiration rate and the heart rate are indicated with green (light color in a grayscale image). Here, if the value approaches the abnormal value, color changes to red or blue. Further, a hatched portion is a non-measurement interval (powered OFF).

That is, if the value becomes a higher value from the normal range, color changes from green to yellow, and then, red. Further, if the value becomes a lower value from the normal range, color changes from green to light blue, and then, blue. In a case of gray scale, color changes from light color to dark color.

Further, also the state of the patient related to whether the patient is sleeping or not can be displayed while being color-coded. For example, "out-of-bed" may be expressed with white, "waking (in-bed)" may be expressed with orange, and "sleeping (in-bed)" may be expressed with blue.

In each drawing, color becomes darker in order of "out-of-bed", "waking (in-bed)" and "sleeping (in-bed)".

Further, in the case where the sleep state is indicated, it is also possible to display the amount of activity together with the state of the patient related to whether the patient is sleeping or not. For example, it is possible to confirm the state of the patient related to whether the patient is sleeping or not and the amount of activity together by a graph indicating the amount of activity being displayed in an overlapped manner with a black vertical bar for overlap display.

Because the biological information value normally shows periodic fluctuation such as daily fluctuation and weekly fluctuation, by utilizing the patient diaries in this manner, it becomes easier to see longer-term fluctuation of the patient, so that there is an advantage that it is possible to notice poor physical condition early. It becomes possible to estimate the state of the patient with high accuracy using the plurality of pieces of diary data. For example, it becomes possible to avoid to accidentally determine the state of the patient as an abnormal state in the case where in a time slot in which the heart rate indicates an abnormal value, there is no change in other biological information values such as respiration rate, in the case where the value indicates an abnormal value in a certain time slot every day, or the like.

It is possible to utilize a plurality of patient diaries. While, normally, an abnormality of the patient is visually determined by a person by utilizing the patient diaries, by utilizing the system of the present embodiment, it becomes possible to automatically and appropriately estimate an abnormality of the patient and make a notification with a fixed criterion which is free from an individual difference and capabilities of determination without taking trouble for visual determination.

4.1. Recovery Example 1

Figure 7:
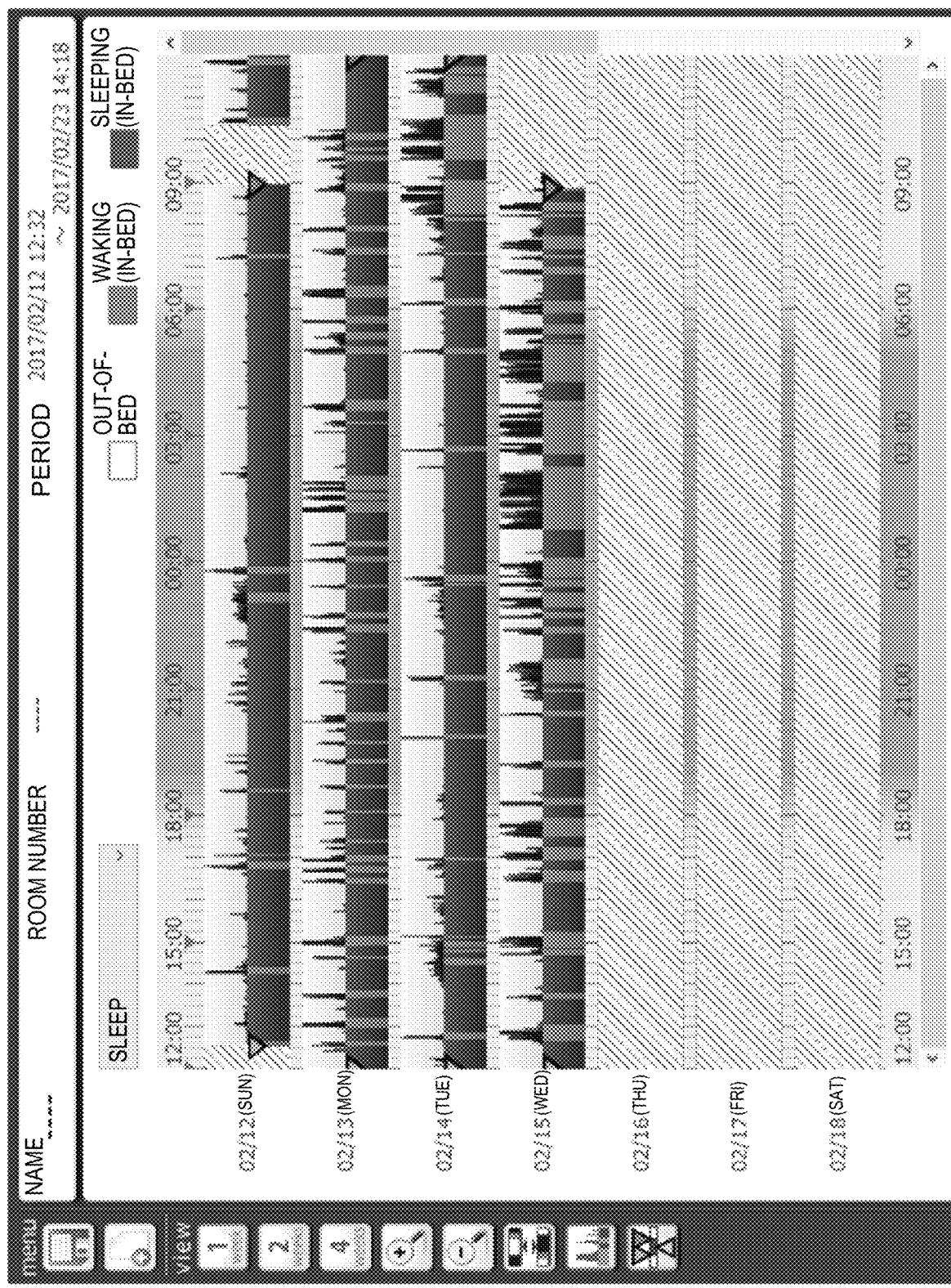
FIG. 7 is a diagram for explaining a patient diary (sleeping diary) as an example.
Figure 8:
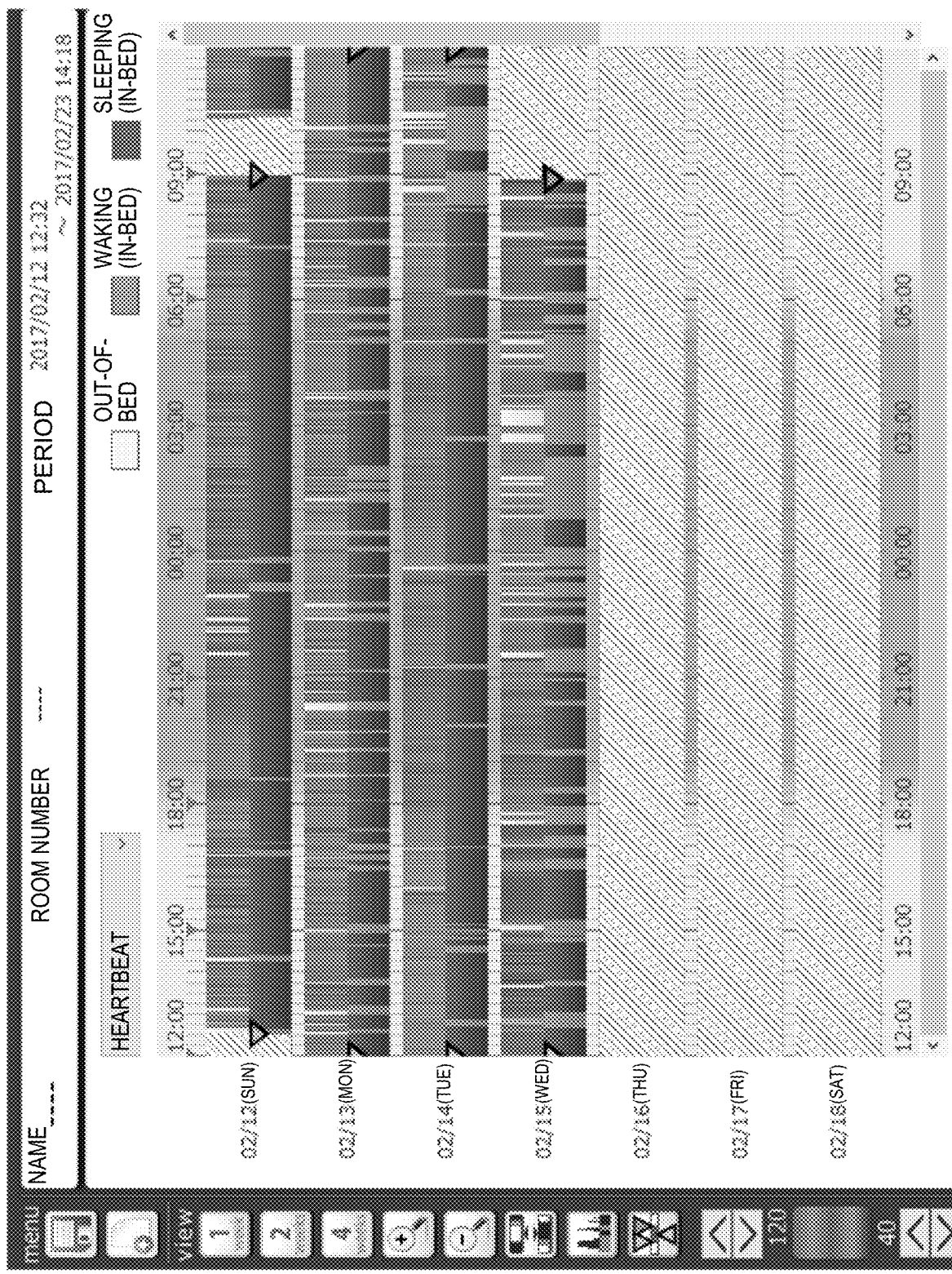
FIG. 8 is a diagram for explaining a patient diary (heartbeat diary) as an example.
Figure 9:
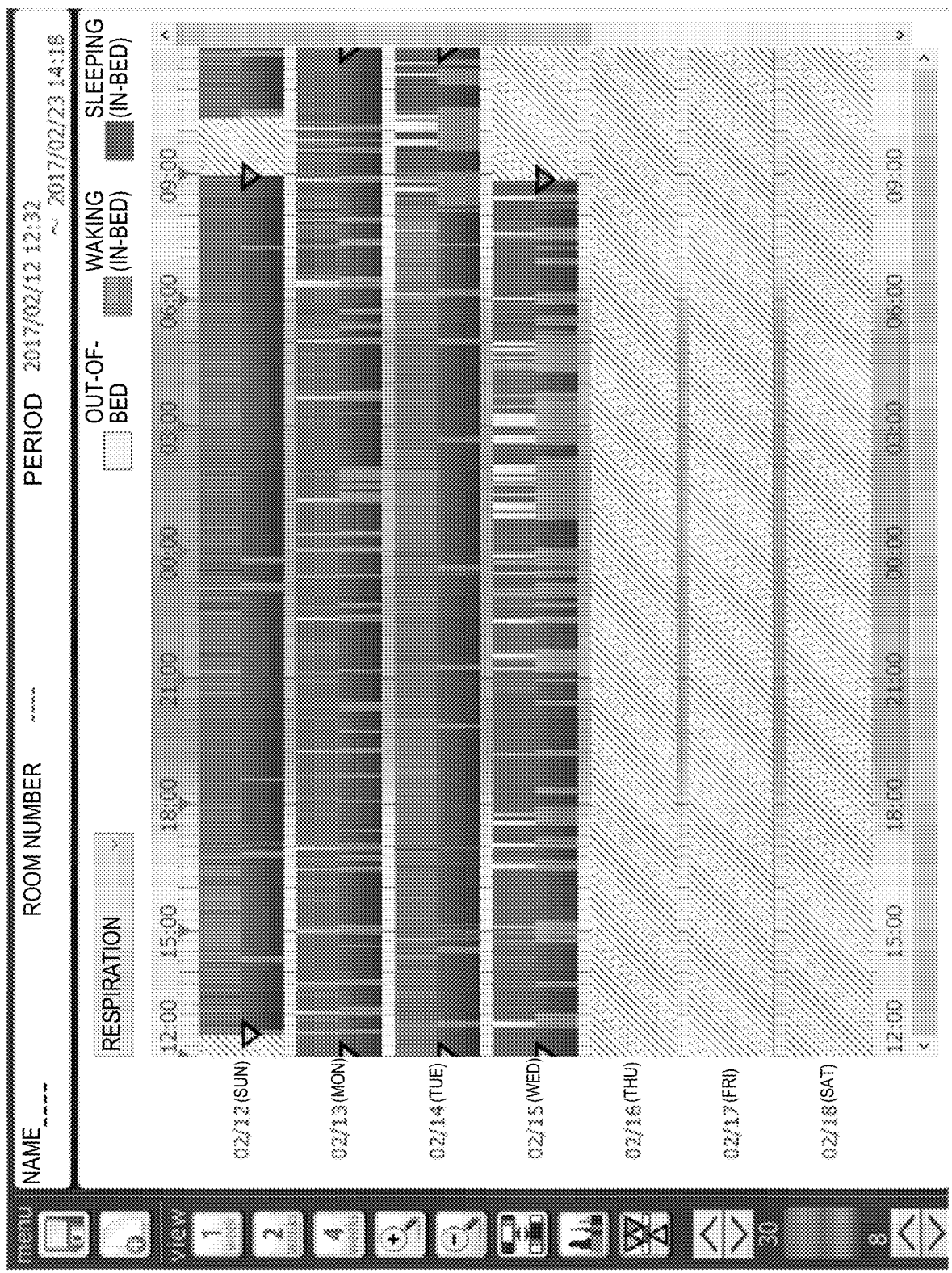
FIG. 9 is a diagram for explaining a patient diary (respiratory diary) as an example.

First, a recovery example 1 will be described as a first example. For example, FIG. 7, FIG. 8 and FIG. 9 are patient diaries of an elderly person who needs care and who lives in a certain nursing home. FIG. 7 is a sleep diary, FIG. 8 is a heartbeat diary, and FIG. 9 is a respiratory diary. An upper part of the graph of the patient diary in FIG. 7 indicates an amount of activity (black vertical bar) and a lower part indicates the state of the patient related to whether the patient is sleeping or not. Further, an upper part of the heartbeat diary in FIG. 8 indicates fluctuation of the heart rate and a lower part indicates the state of the patient related to whether the patient is sleeping or not, and an upper part of the respiratory diary in FIG. 9 indicates fluctuation of the respiration rate and a lower part indicates the state of the patient related to whether the patient is sleeping or not.

Here, because, in the patient diaries, one line corresponds to 24 hours, and the center of the graph indicates midnight, date changes at the center of the graph. The patient diaries from February 12, Sunday are indicated, and the graphs show a state where the patient recovers and leaves the hospital around 9:00 on February 16, Thursday.

Referring to the respiration rate in FIG. 9, dark color (abnormal value) is shown a number of times from February 12 to February 14. Further, referring to the heart rate in FIG. 8, dark color (abnormal value) is shown a number of times from the morning of February 14.

It is therefore possible to determine that physical condition of the patient is poor at this time. Thereafter, referring to February 14 to February 16, the respiration rate and the heart rate come to fall within the normal ranges. Further, referring to the sleep diary in FIG. 7, a large amount of activity is calculated from February 14 to February 16. That is, at this time point, the activity amount determination conditions are not satisfied.

Because the biological information values come to fall within the normal ranges, and a number of times of motion of the patient can be observed, it is determined that the patient is recovering.

4.2. Recovery Example 2

Figure 10:
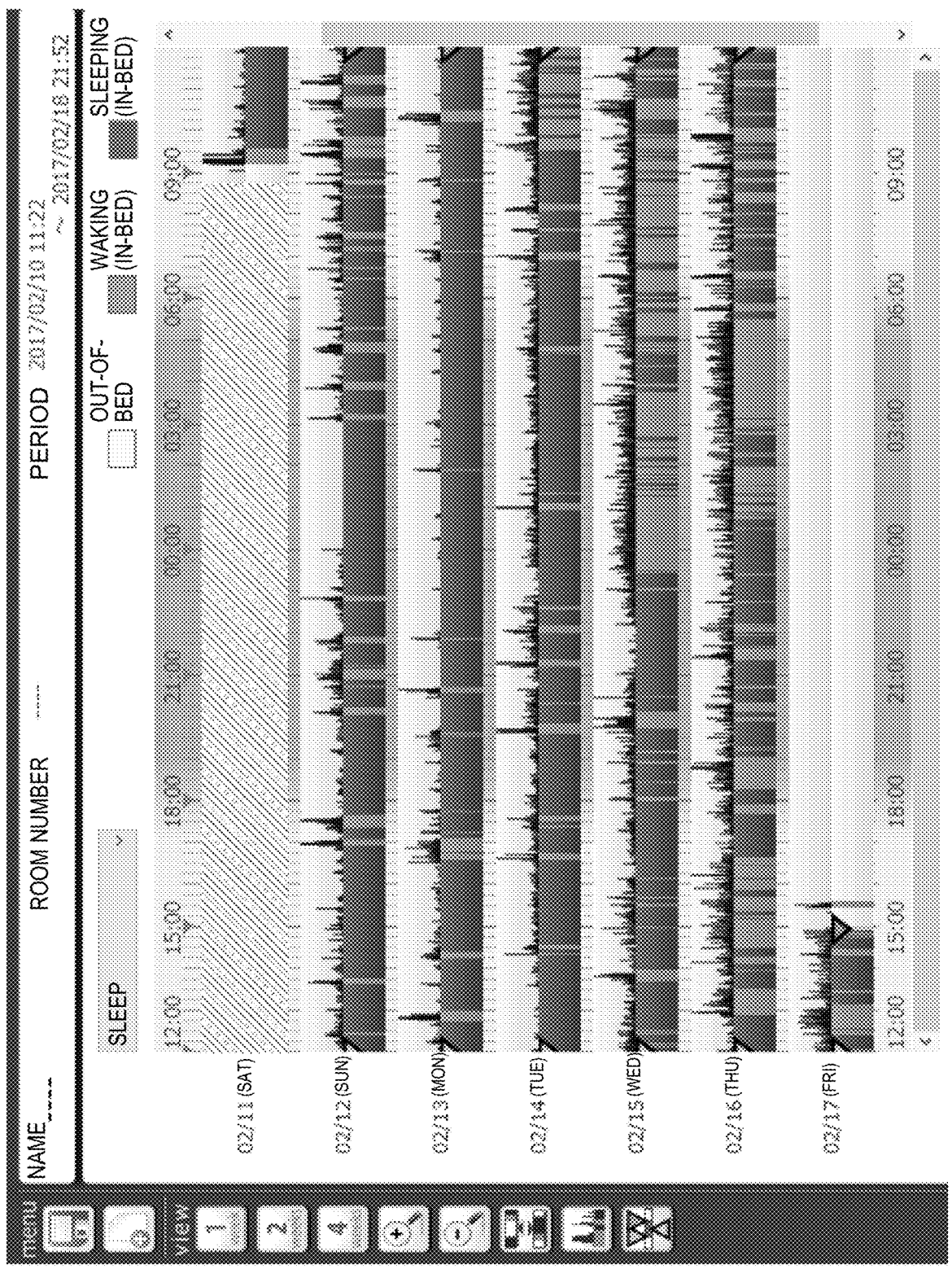
FIG. 10 is a diagram for explaining a patient diary (sleeping diary) as an example.

Subsequently, a recovery example 2 will be described as a second example. In the recovery example 2, FIG. 10 is a sleep diary, FIG. 11 is a heartbeat diary, and FIG. 12 is a respiratory diary.

Here, in the patient diary, one line corresponds to 24 hours, and the center of the graph indicates midnight. The patient is in-bed and the patient diary is indicated from February 12, Sunday, and the graphs show a state where the patient recovers and leaves the hospital in the afternoon of February 17, Friday.

Figure 11:
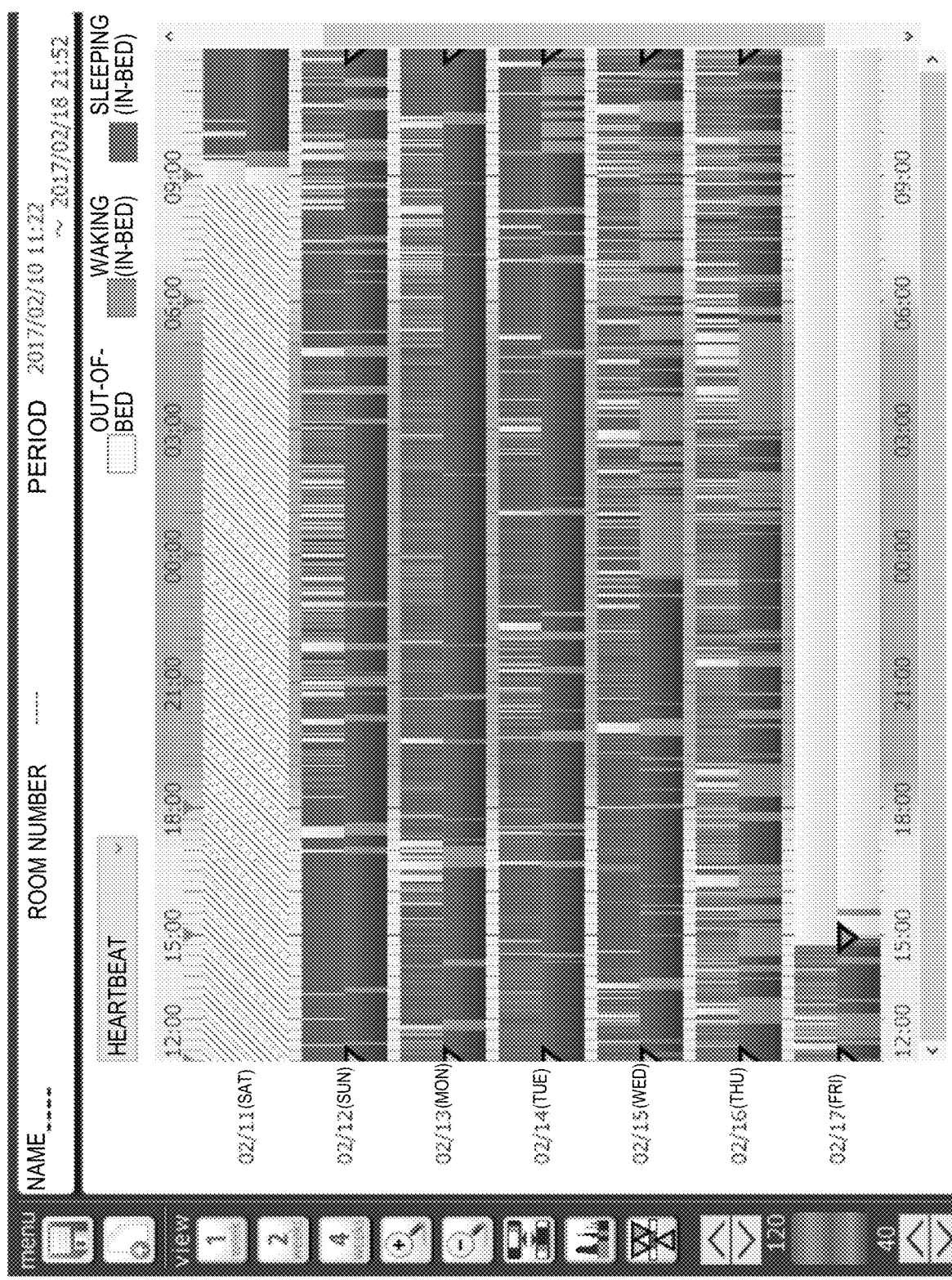
FIG. 11 is a diagram for explaining a patient diary (heartbeat diary) as an example.
Figure 12:
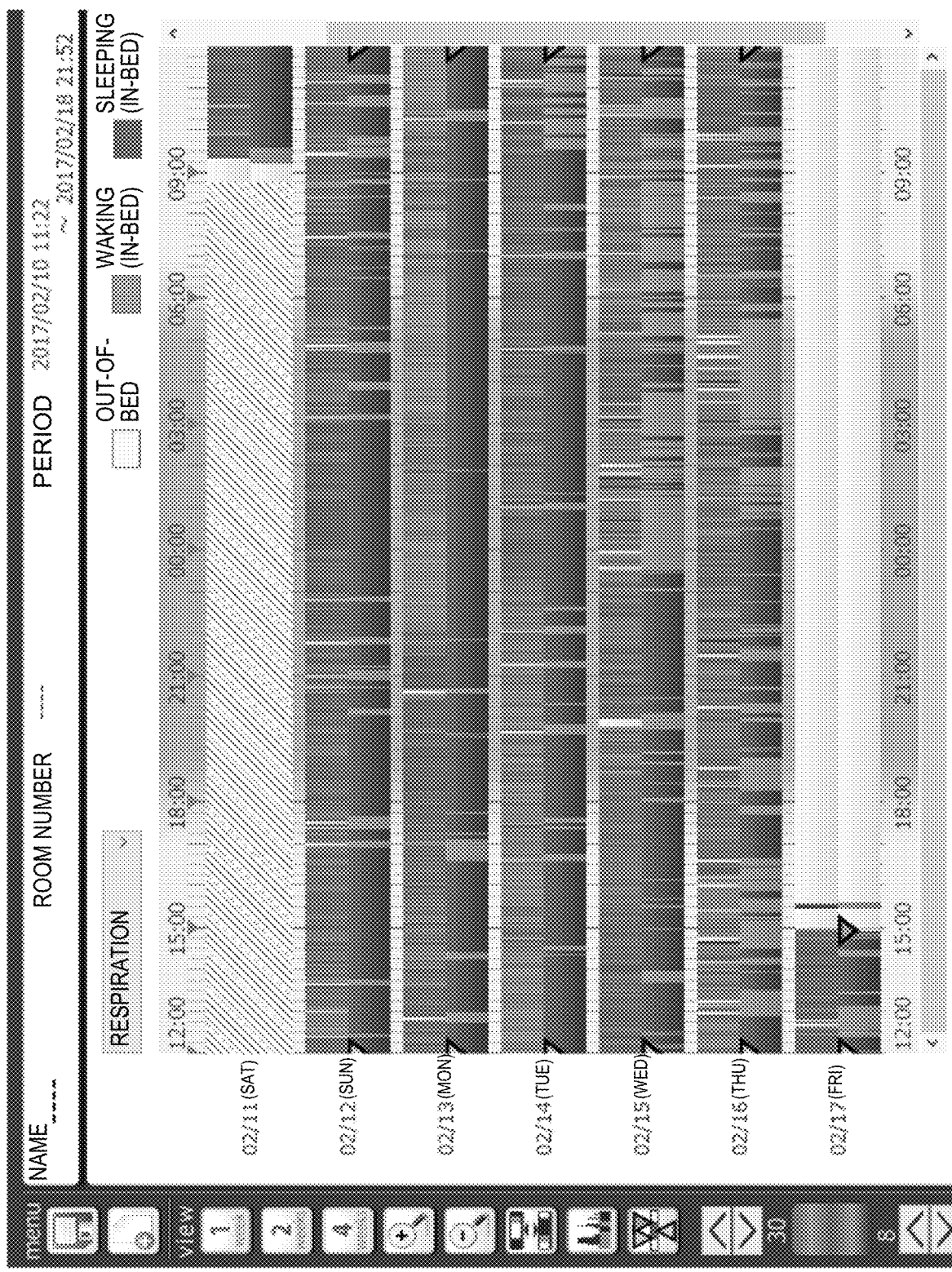
FIG. 12 is a diagram for explaining a patient diary (respiratory diary) as an example.

Referring to FIG. 11, the heart rate prominently shows an abnormal value from February 11, Saturday until the morning of February 16, Thursday. However, the heart rate comes to fall within the normal range from the afternoon of February 16, Wednesday to February 17, Friday.

Further, after February 16, Thursday, the respiration rate becomes stable, and the biological information values (the heart rate and the respiration rate) come to fall within the normal ranges. Further, referring to FIG. 10, a large amount of activity is detected also on and after February 16, Thursday.

Therefore, while the biological information values fall within the normal ranges, because the amount of activity (an average amount of activity) which is one of the activity amount determination conditions is equal to or higher than a determined threshold, it is not determined that the patient comes close to death. It is therefore determined that the patient is recovering in a case of the patient of the present drawings.

4.3. Death Example 1

Figure 13:
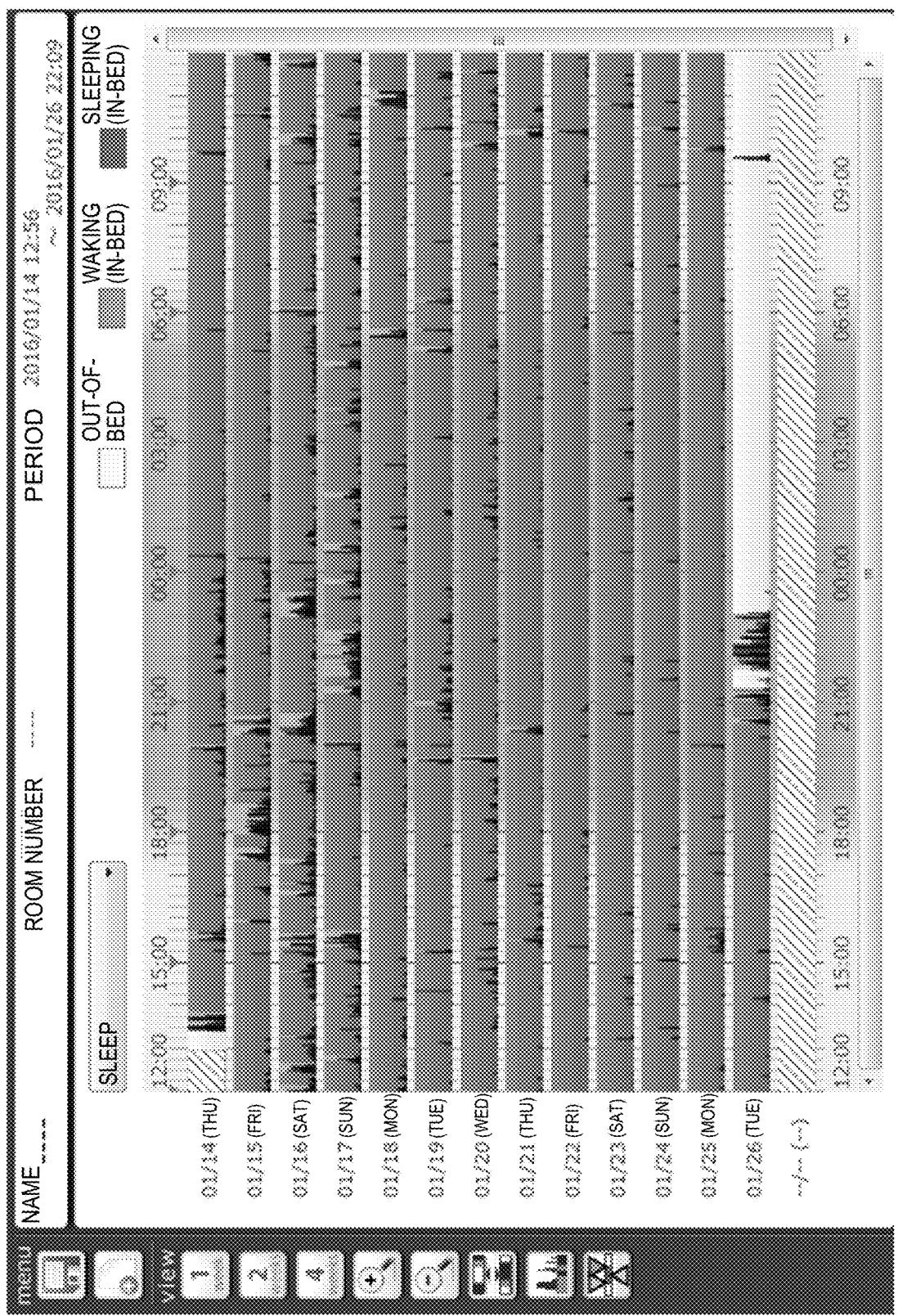
FIG. 13 is a diagram for explaining a patient diary (sleeping diary) as an example.
Figure 14:
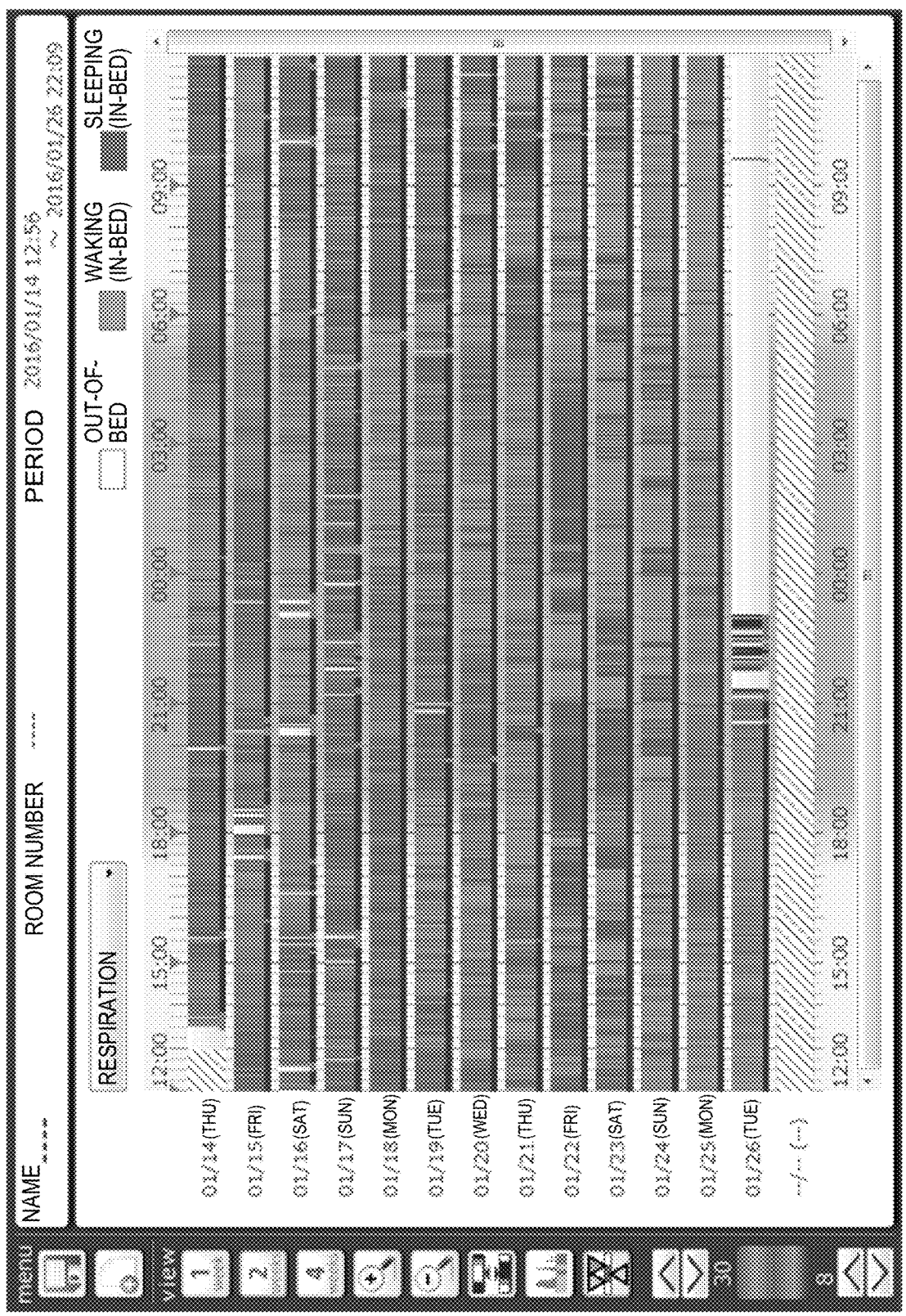
FIG. 14 is a diagram for explaining a patient diary (respiratory diary) as an example.
Figure 15:
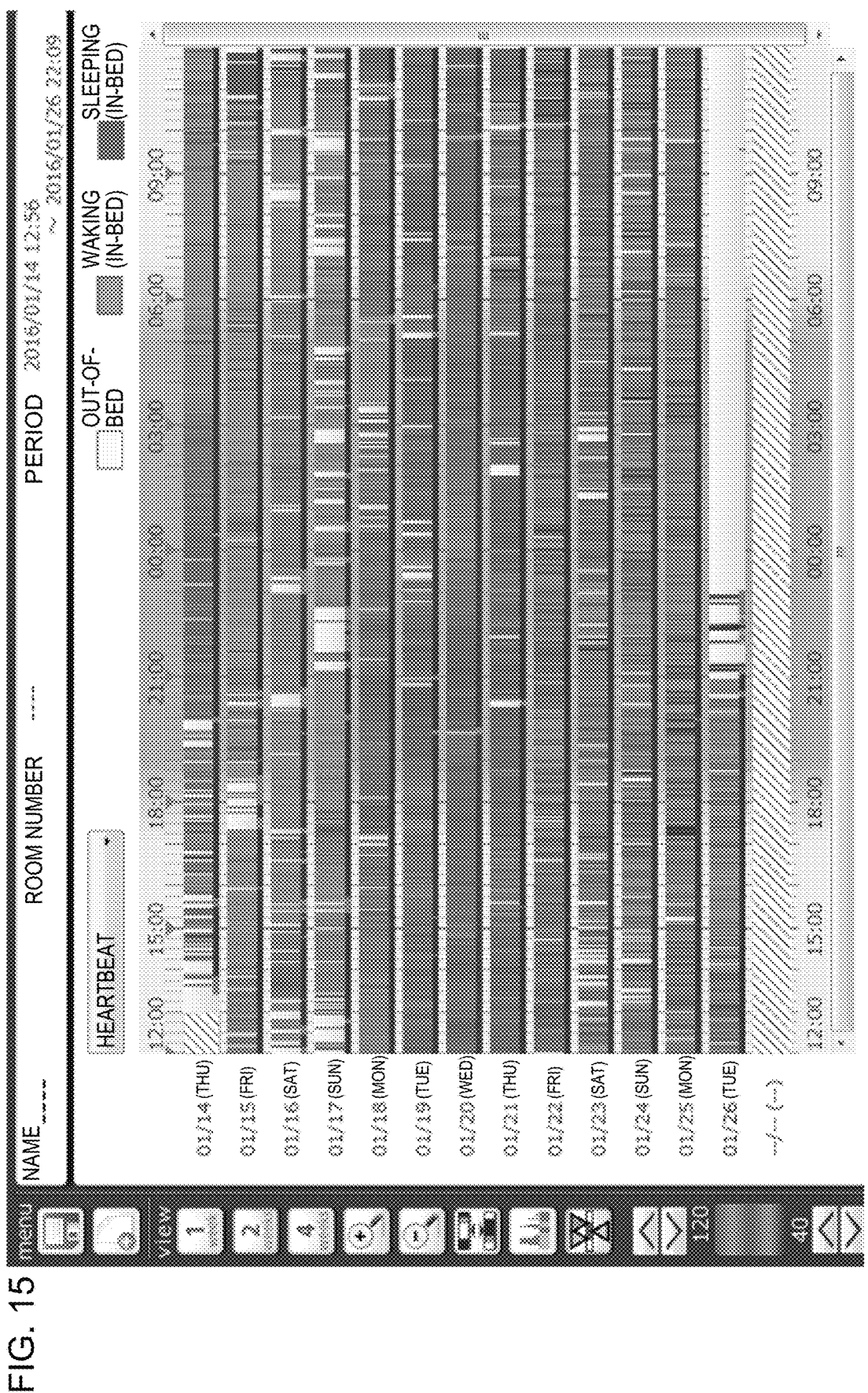
FIG. 15 is a diagram for explaining a patient diary (heartbeat diary) as an example.

Subsequently, a death example 1 will be described as a third example. In the death example 1, FIG. 13 is a sleep/activity amount diary, FIG. 14 is a sleep diary, and FIG. 15 is a heartbeat diary. In FIG. 13, the state of the patient related to whether the patient is sleeping or not and the amount of activity are displayed in an overlapped manner. That is, a black vertical bar indicates an amount of activity.

Here, in the respiratory diary in FIG. 14, the respiration rate of the patient increases from the afternoon of January 21, Friday, and an abnormal value is detected. This abnormal value is shown until around 3 a.m. of January 26, Tuesday, and the value comes to fall within the normal range thereafter.

Further, in the heartbeat diary in FIG. 15, the heart rate becomes low from around January 23, Saturday, and an abnormal value is detected. Then, the value comes to fall within the normal range from around 3 a.m. of January 26, Tuesday.

While the biological information values fall within the normal ranges from around 3 a.m. of January 26, Tuesday, referring to the sleep diary in FIG. 13, out-of-bed is not detected after 3 a.m. Further, it can be seen that the amount of activity is low and the patient does not practically move.

Therefore, because the activity amount determination conditions are satisfied, it is determined that the patient comes close to death. At this time, it is also possible to perform processing of making a notification or activate the alarm that the patient comes close to death. For example, it is also possible to display that the patient comes close to death at a display apparatus or output an alert or activate the alarm using light and sound. Further, it is also possible to transmit an e-mail or transmit a notification signal or activate the alarm to a terminal apparatus of a medical personnel.

4.4. Death Example 2

Figure 16:
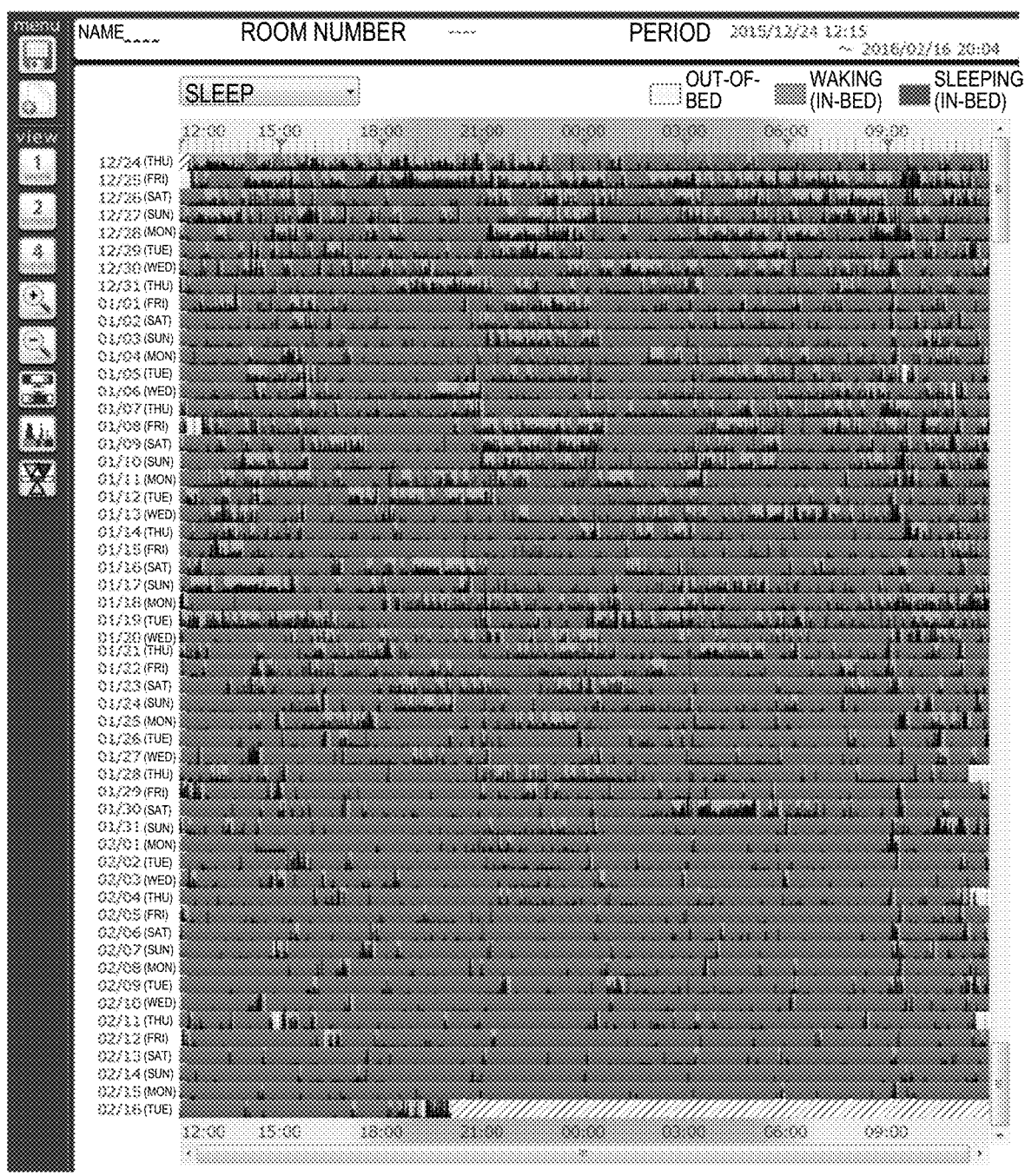
FIG. 16 is a diagram for explaining a patient diary (sleeping diary) as an example.
Figure 17:
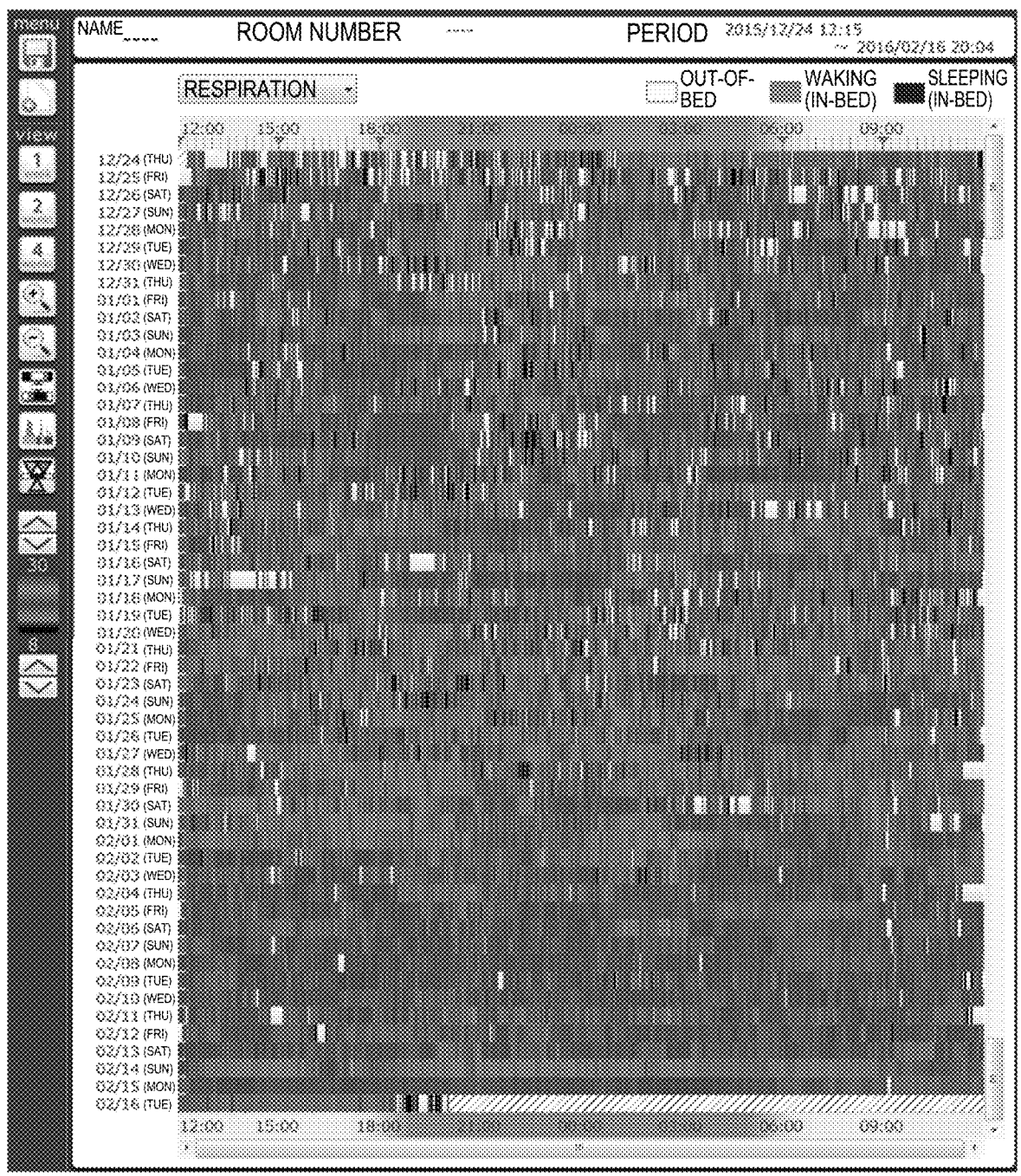
FIG. 17 is a diagram for explaining a patient diary (respiratory diary) as an example.
Figure 18:
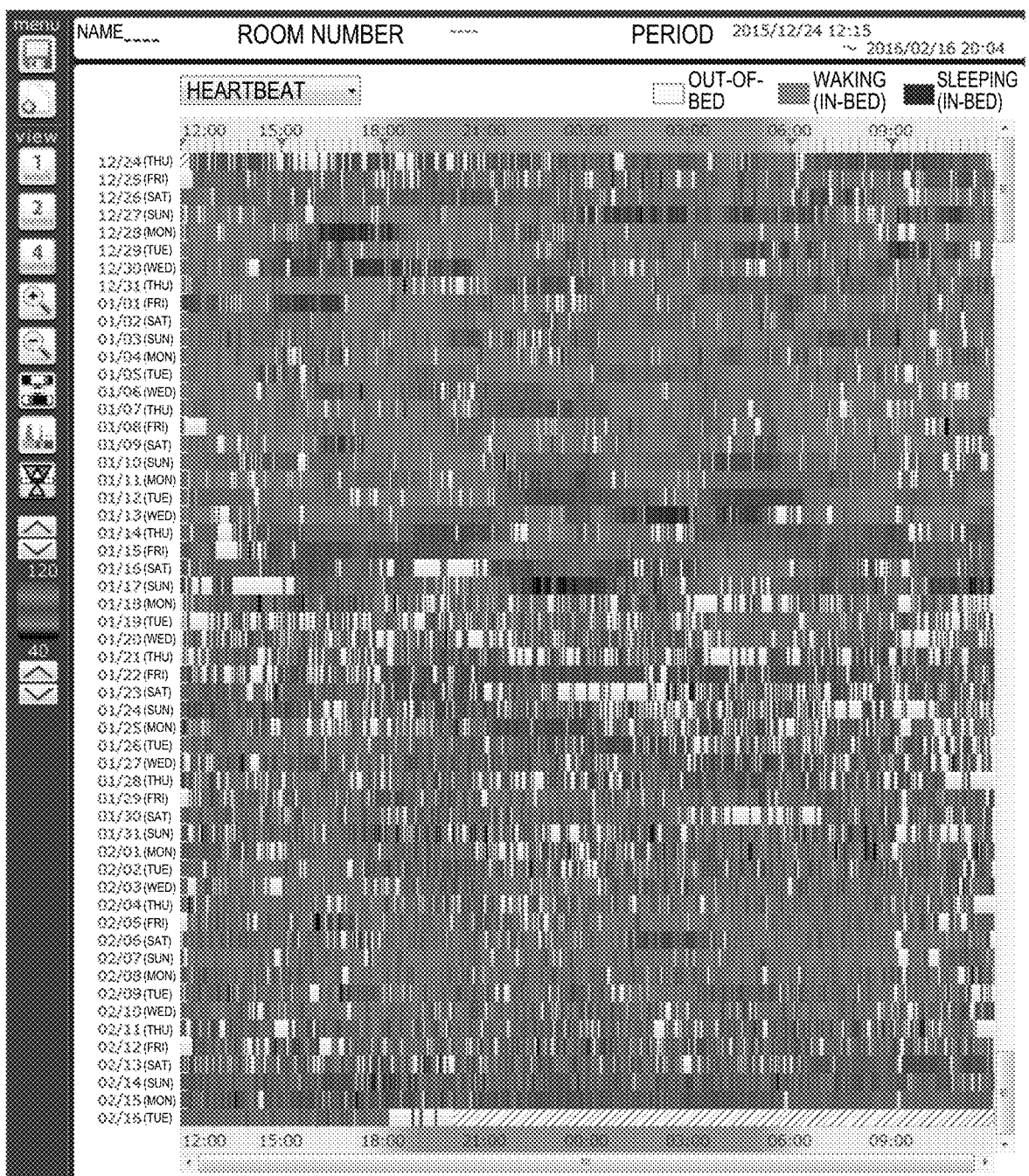
FIG. 18 is a diagram for explaining a patient diary (heartbeat diary) as an example.

Subsequently, a death example 2 will be described as a fourth example. In the death example 2, FIG. 16 is a sleep/activity amount diary, FIG. 17 is a respiratory diary, and FIG. 18 is a heartbeat diary. In FIG. 16, the sleep state and the amount of activity are displayed in an overlapped manner. That is, the amount of activity is displayed with a black vertical bar.

In the heartbeat diary in FIG. 18, the abnormal value becomes prominent from around January 21, Thursday, and it can be determined that physical condition is poor. Here, the heart rate comes to fall within the normal range from the afternoon of February 14, Sunday.

Further, in the respiratory diary in FIG. 17, the value comes to substantially fall within the normal range on and after February 2, Tuesday. Therefore, because the heart rate and the respiration rate come to fall within the normal ranges from the afternoon of February 14, Sunday, it seems that the patient is recovering.

However, referring to the sleep/activity amount diary in FIG. 16, the patient does not go out-of-bed, the sleeping state continues, and the amount of activity is low (it can be considered that the amount of activity which can be observed in part is not the activity by the patient, but mainly the activity by a helper). That is, for 12 hours which are the second determination time period, the biological information values fall within the normal ranges, and out-of-bed is not determined. Further, because the amount of activity is low, the activity amount determination conditions are satisfied.

Therefore, it is determined that the patient comes close to death and a notification is made. In this manner, according to the present embodiment, even in the case where it is determined that the state of the patient is a recovering state (the patient is recovering) only from the biological information values, it is possible to correctly determine that the patient comes close to death.

Further, by making a notification that it is determined that the patient comes close to death, for example, a medical personnel and family members can be by the patient's bedside when the patient dies.

5. Modified Examples

While the embodiments have been described in detail above with reference to the drawings, the specific configuration is not limited to the embodiments, and design, or the like, which are within the scope not deviating from the gist of the present invention are included in the claims.

Further, while, in the present embodiment, the biological information is output from the processing apparatus 5 on the basis of the result output from the detection apparatus 3, the detection apparatus 3 may perform all calculation. Further, as well as a configuration where application is installed and implemented at a terminal apparatus (for example, a smartphone, a tablet and a computer), it is, for example, also possible to perform processing on the server side and return the processing result to the terminal apparatus.

For example, the above-described processing may be executed on the server side by the biological information being uploaded to the server from the detection apparatus 3. The detection apparatus 3 may be implemented by an apparatus such as a smartphone in which, for example, an acceleration sensor and a vibration sensor are incorporated.

Further, a program running at each apparatus in the present embodiment is a program of controlling a CPU, or the like, (a program for causing a computer to function) to execute the functions of the above-described embodiments. Information handled at these apparatuses is temporarily accumulated in a temporal storage apparatus (for example, a RAM) upon the processing, and, then, stored in a storage apparatus such as various kinds of ROMs, HDDs and SSDs, and read out, corrected and written by the CPU as necessary.

Further, in the case where the program is distributed to the market, it is possible to distribute the program stored in a portable recording medium, or forward the program to a server computer connected via a network such as the Internet. In this case, the storage apparatus of the server computer is, of course, also included in the present invention.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An apparatus comprising:
   a sensor configured to acquire a biological signal of a user, wherein the sensor is further configured to sense an activity amount of the user; and
   a controller configured to:
      determine whether a value of the biological signal is continuously outside a predetermined normal range for a first time period;
      after determining that the value of the biological signal has been continuously outside the predetermined normal range for the first time period, then determine whether the value of the biological signal is inside the predetermined normal range; and
      determine that the user is approaching an onset of death and activate an alarm indicating that the user is approaching the onset of death when:
         the controller determines that the value of the biological signal is outside the predetermined normal range for the first time period, and the value of the biological signal is continuously inside the predetermined normal range for a second time period, the second time period being longer than the first time period, and
         the controller determines that the activity amount of the user is lower than a predetermined threshold.

2. The apparatus according to claim 1, wherein the controller is configured to determine that the user is approaching the onset of death when the controller has determined that the biological signal has been outside the predetermined normal range for the first time period, the biological signal has been continuously inside the predetermined normal range for the second time period, and the activity amount is lower than a threshold during the second time period.

3. The apparatus according to claim 1, wherein the controller is configured to determine whether the user is out of bed based on the activity amount and to determine that the user is approaching the onset of death when the controller has determined that the biological signal has been outside the predetermined normal range for the first time period, the biological signal has been continuously inside the predetermined normal range for the second time period, the activity amount is lower than a threshold during the second time period and the user is not out of bed.

4. The apparatus according to claim 1, wherein the controller is configured to determine a biological information value from the biological signal.

5. The apparatus according to claim 4, wherein the controller is configured to determine a heart rate and a respiration rate of the user as the biological information value.

6. The apparatus according to claim 1, wherein the sensor is configured to acquire the biological signal without any contact between the sensor and the user.

7. A method comprising:
acquiring with a sensor a biological signal of a user and an activity amount of the user; and
determining, with a controller, whether a value of the biological signal is continuously outside a predetermined normal range of biological signal values for a first time period;
determining, with the controller, that the value of the biological signal has been continuously outside the predetermined normal range for the first time period, and then determining whether the value of the biological signal is inside the predetermined normal range;
determining with the controller that the user is approaching an onset of death by:
determining that the value of the biological signal is outside the predetermined normal range for the first time period, and the value of the biological signal is continuously inside the predetermined normal range for a second time period, the second time period being longer than the first time period, and determining that the activity amount of the user is lower than a predetermined threshold; and, in response,
activating, with the controller, an alarm indicating that the user is approaching the onset of death.

8. The method according to claim 7, comprising:
determining that the user is approaching the onset of death when it is determined that the biological signal has been outside the predetermined normal range for the first time period, the biological signal has been continuously inside the predetermined normal range for the second time period, and the activity amount is lower than a threshold during the second time period.

9. The method according to claim 7, further comprising:
determining with the controller whether the user is out of bed based on the activity amount, and determining that the user is approaching the onset of death when it is determined that the biological signal has been outside the predetermined normal range for the first time period, the biological signal has been continuously inside the predetermined normal range for the second time period, the activity amount is lower than a threshold during the second time period and the user is not out of bed.

10. The method according to claim 7, further comprising:
determining with the controller a biological information value from the biological signal.

11. The method according to claim 10, further comprising:
determining with the controller a heart rate and a respiration rate of the user as the biological information value.

12. The method according to claim 7, wherein the acquiring of the biological signal is done without any contact between the sensor and the user.

13. A non-transitory computer readable medium having stored thereon a program for causing a microprocessor to execute the following:
acquiring with a sensor a biological signal of a user and an activity amount of the user; and
determining, with a controller, whether a value of the biological signal is continuously outside a predetermined normal range of biological signal values for a first time period;
determining, with the controller, that the value of the biological signal has been continuously outside the predetermined normal range for the first time period, and then determining whether the value of the biological signal is inside the predetermined normal range;
determining with the controller that the user is approaching an onset of death by:
determining that the value of the biological signal is outside the claimed invention as previously noted in the discussion of claims predetermined normal range for the first time period, and the value of the biological signal is continuously inside the predetermined normal range for a second time period, the second time period being longer than the first time period, and determining that the activity amount of the user is lower than a predetermined threshold; and, in response,
activating, with the controller, an alarm indicating that the user is approaching the onset of death.

* * * * *